(12) United States Patent
Kadayam Viswanathan et al.

(10) Patent No.: US 9,720,128 B2
(45) Date of Patent: Aug. 1, 2017

(54) ROTATING FRAME PULSED NUCLEAR MAGNETIC RESONANCE SPECTROSCOPY

(71) Applicant: SCHLUMBERGER TECHNOLOGY CORPORATION, Sugar Land, TX (US)

(72) Inventors: Ravinath Kausik Kadayam Viswanathan, Somerville, MA (US); Lukasz Zielinski, Houston, TX (US); Martin D. Hürlimann, Newton, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 1172 days.

(21) Appl. No.: 13/768,965

(22) Filed: Feb. 15, 2013

(65) Prior Publication Data
US 2014/0232391 A1   Aug. 21, 2014

(51) Int. Cl.
*G01V 3/00*   (2006.01)
*G01V 3/32*   (2006.01)
(Continued)

(52) U.S. Cl.
CPC ............. *G01V 3/32* (2013.01); *G01N 24/081* (2013.01); *G01R 33/448* (2013.01); *G01R 33/4633* (2013.01)

(58) Field of Classification Search
CPC ................................................ G01R 33/4633
USPC .................................. 324/303, 307, 306, 309
See application file for complete search history.

(56) References Cited

U.S. PATENT DOCUMENTS 5,049,820 A * 9/1991 Briand ............... G01R 33/4833
                                                        324/309
5,317,264 A * 5/1994 Rommel ............. G01R 33/446
                                                        324/307
(Continued)

OTHER PUBLICATIONS

Jones, "Spin-Lattice Relaxation in the Rotating Frame: Weak-Collision Case," Physical Review, Aug. 1966, vol. 148(1): pp. 332-335.
(Continued)

*Primary Examiner* — Louis Arana
(74) *Attorney, Agent, or Firm* — Bridget M. Laffey

(57) ABSTRACT

An NMR method and apparatus for analyzing a sample of interest applies a static magnetic field together with RF pulses of oscillating magnetic field across a sample volume that encompasses the sample of interest. The RF pulses are defined by a pulse sequence that includes a plurality of measurement segments configured to characterize a plurality of relaxation parameters related to relaxation of nuclear magnetization of the sample of interest. Signals induced by the RF pulses are detected in order to derive the relaxation parameters. The measurement segments of the pulse sequence include at least one first-type measurement segment configured to characterize relaxation of spin-lattice interaction between nuclei of the sample of interest in a rotating frame ($T_{1\rho}$) at a predefined frequency. The $T_{1\rho}$ parameter can be measured in conjunction with the measurement of other relaxation and/or diffusion parameters as part of multidimensional NMR experiments.

34 Claims, 12 Drawing Sheets

(51) Int. Cl.
    G01R 33/46      (2006.01)
    G01N 24/08      (2006.01)
    G01R 33/44      (2006.01)

(56) References Cited

U.S. PATENT DOCUMENTS

| | | | |
|---|---|---|---|
| 7,486,070 B2 | 2/2009 | Madio et al. | |
| 2006/0244447 A1* | 11/2006 | Michaeli | G01R 33/50 324/309 |
| 2013/0234706 A1* | 9/2013 | Mandal | G01N 24/081 324/303 |
| 2016/0077026 A1* | 3/2016 | Pusiol | G01N 24/08 324/306 |

OTHER PUBLICATIONS

Kimmich et al., "Field-cycling NMR relaxometry," Progress in Nuclear Magnetic Resonance Spectroscopy, 2004, vol. 44: pp. 257-320.

Look et al., "Nuclear Magnetic Dipole-Dipole Relaxation Along the Static and Rotating Magnetic Fields: Application to Gypsum," The Journal of Chemical Physics, vol. 44(8): pp. 2995-3000.

McDonald et al., "Surface relaxation and chemical exchange in hydrating cement pastes:A two-dimensional NMR relaxation study," Physical Review E, 2005, vol. 72: pp. 014409-1-011409-9.

Qiao et al., "Diffusion exchange NMR spectroscopic study of dextran exchange through polyelectrolyte multilayer capsules," The Journal of Chemical Physics, 2005, vol. 122: pp. 214912-1-214912-9.

Song et al., "T1-T2 Correlation Spectra Obtained Using a Fast Two-Dimensional Laplace Inversion," Journal of Magnetic Resonance, 2002, vol. 154: pp. 261-268.

Washburn et al., "Tracking Pore to Pore Exchange Using Relaxation Exchange Spectroscopy," Physical Review Letters, Oct. 2006, vol. PRL 97: pp. 175502-1-175502-4.

Kausik, et al., "Multidimensional Rotating Frame Correlation of Relaxation Dispersion", 10th Bologna Conference on Magnetic Resonance in Porous Media, Sep. 12-16, 2010, p. 26-27.

* cited by examiner $\omega 1 = 8928$ Hz  $\omega 2 = 1562$ Hz

ROTATING FRAME PULSED NUCLEAR MAGNETIC RESONANCE SPECTROSCOPY

FIELD

This application relates to instruments making use of nuclear magnetic resonance (NMR) techniques for evaluating characteristics of properties of samples.

BACKGROUND

NMR experiments that measure multidimensional correlations of relaxation and diffusion properties like $T_1$-$T_2$, D-$T_2$ have been established as valuable methodologies for the identification of molecular species and understanding their dynamics. These experiments are similar to multidimensional NMR spectroscopic methods but involve the inverse Laplace transformation (or other inversion techniques) to study relaxation and diffusion properties which are associated with exponential decays. The advantages of such a multidimensional approach over the use of one dimensional $T_1$ and $T_2$ relaxation times or diffusion properties has been clearly shown.

The complete frequency dependence of spin-lattice relaxation time $T_1$ can be measured using the field cycling relaxation technique. This is generally done in an electromagnet whose field is controlled by the current passed through the coil. These experiments are technology and hardware intensive. While field cycling relaxometry is a powerful method to measure relaxation dispersion, some of its disadvantages include the complexity of the technology and associated hardware, the field inhomogeneity of the electromagnets and the impracticality of measuring systems in-situ, especially in a space-constrained downhole environment typical of well logging applications.

Recently, the $T_1$-$T_1$ correlation between $T_1$ distributions at two different Larmor frequencies was studied in a novel way using fast-field cycling relaxometry. This technique enables the study of correlations between different components of the relaxation distributions at each frequency, which is subsequently plotted and well highlighted in a two-dimensional plot. The pulse sequence for measuring the $T_1$-$T_1$ correlation is shown in FIG. 1A and the corresponding results on a heavy crude oil sample is shown in FIG. 1B. The disadvantage is that such experiments can be carried out only in field cycling relaxometry instruments which provide for variation of the magnetic field $B_0$ to obtain the frequency (or magnetic field) dependence of the $T_1$ relaxation time. Downhole NMR tools and core analysis magnets generally employ a magnetic assembly that provides a static magnetic field $B_0$ that operates at a single frequency, making it impossible to carry out these experiments without major instrumental changes. In downhole NMR tools, due to the magnetic field gradient away from the tool, different slices resonate at different frequencies making possible multi-frequency experiments. The disadvantage of performing these experiments in a downhole NMR tool is that the different frequency measurements are made at different positions in space and thus would be difficult to interpret when formation heterogeneities exist. Also the experiments can be measured only at frequencies to which the antennas are tuned.

$T_1$-$T_2$ correlation experiments have been regularly carried out in the oil and gas industry as they give information about correlations between Larmor frequency and low frequency dynamics. Thus fluids which are motionally narrowed have $T_1$=$T_2$ and would appear on the diagonal line. But fluids which exhibit motions at or below the Larmor frequency like heavy oils or oils with asphaltene in them would show dispersion at these frequencies. The fluids that exist in small pores would also be slowed down by the interaction with the surfaces of the confining pores and exhibit slow motions. The presence of these slow motions results in these fluids exhibiting signals that are off the diagonal (as $T_1$>$T_2$). For example the bitumen found in organic shale has a $T_1$-$T_2$ ratio of 6 to 10 while heavy oils with asphaltene have $T_1$-$T_2$ ratios from 1.5 to 3.5, while bulk water and light oils have $T_1$-$T_2$ ratios that range from 1 to 1.5.

The spin lattice relaxation time in the rotating frame $T_{1\rho}$ is an alternative method to study the relaxation behavior as a function of frequency. The pulse sequence for measuring $T_{1\rho}$ at one particular frequency is given in FIG. 2. It involves a 90 degree pulse in the x direction (labeled $90_x$) followed by a spin lock pulse in the y direction (labeled $SL_y$). The magnitude of the spin lock pulse dictates the frequency $\omega_1$ of the spin lock field. The magnitude of the spin lock pulse (and thus the frequency $\omega_1$ of the spin lock field) is fixed over the suite of NMR measurements. The duration (labeled $\tau_R$) of the spin lock pulse can be varied over the suite of NMR measurements. The NMR signal (labeled $AQ_y$) that follows the spin lock pulse for each pulse sequence of the suite is processed to obtain a $T_{1\rho}$ value.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Embodiments are provided for NMR analysis of a sample of interest. A static magnetic field is applied across a sample volume that encompasses the sample of interest. RF pulses of oscillating magnetic field are produced across the sample volume. The RF pulses are characterized by a direction in a plane transverse to the static magnetic field. The RF pulses are defined by a pulse sequence that includes a plurality of measurement segments that are configured to characterize a plurality of relaxation and/or diffusion parameters related to the nuclear magnetization of the sample of interest. Signals induced by the RF pulses of oscillating magnetic field are detected in order to derive the plurality of relaxation and/or diffusion parameters. The plurality of measurement segments of the pulse sequence include at least one first-type measurement segment that is configured to characterize relaxation of spin-lattice interaction between nuclei of the sample of interest in a rotating frame ($T_{1\rho}$) at a predefined frequency. The $T_{1\rho}$ parameter can be measured in conjunction with the measurement of other relaxation parameters (such as $T_{1\rho}$ at a different frequency and/or $T_2$ and/or $T_1$ and/or diffusion) as part of multidimensional NMR experiments.

The multidimensional NMR experiments of the present application are based on relaxation in the rotating frame that can be used to study low frequency dispersion dynamics of various systems. Many systems including but not limited to fluids in porous media, food materials, colloidal aggregation, protein dynamics and heavy oils exhibit motions at low frequencies, especially from 1000 Hz to 100 KHz. The frequency dependence of the relaxation times in this range has unique information about system dynamics. Such information is not available by probing one single frequency and thus dispersion measurements are important. The rotating frame (or $T_{1\rho}$) based NMR experiments of the present application have the potential to better evaluate the fluids and understand the slow motions due to interaction with surfaces. Accordingly, in one embodiment, these pulse sequences have direct applications for fluid typing and wettability characterization. Such NMR experiments can be used in downhole NMR tools and laboratory NMR tools for oilfield applications.

Additional advantages will become apparent to those skilled in the art upon reference to the detailed description taken in conjunction with the provided figures.

DETAILED DESCRIPTION

Figure 1A:
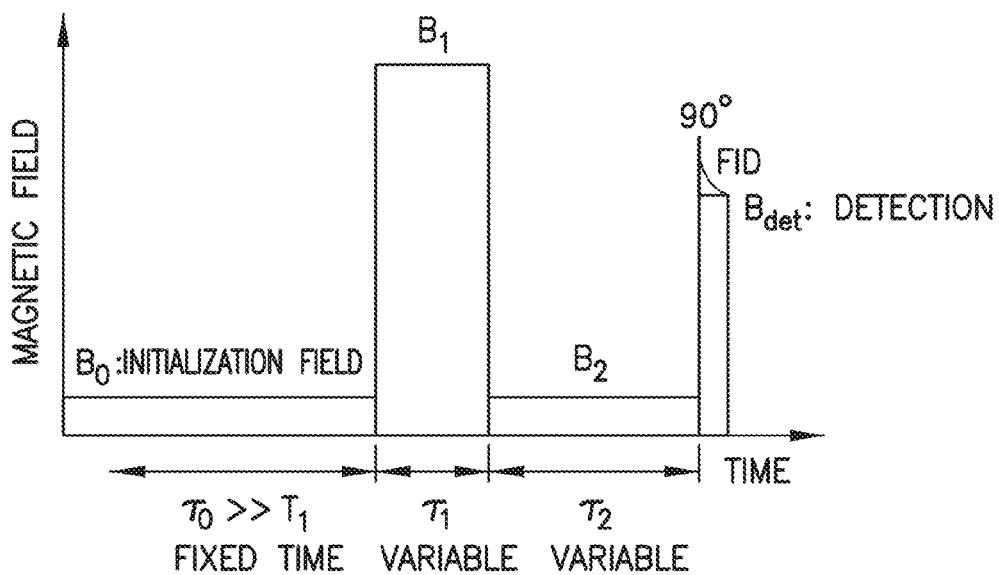
FIG. 1A is a schematic diagram illustrating a prior art NMR pulse sequence used to obtain a $T_1$-$T_1$ correlation distribution.

Embodiments of the present application relate to apparatus and methods for determining properties of a sample using NMR measurements. The NMR measurements carried out by the NMR spectrometer rely upon the fact that the nuclei of many chemical elements have angular momentum ("spin") and a magnetic moment. In the externally applied static magnetic field $B_0$, the spins of nuclei align themselves along the direction of the static magnetic field $B_0$. This equilibrium situation can be disturbed by a pulse of an oscillating magnetic field $B_1$ that tips the spins away from the direction of the static magnetic field $B_0$. For example, if a pulse of alternating current having a frequency f is passed through an RF antenna coil producing the oscillating polarizing magnetic field $B_1$ perpendicular to the static magnetic field $B_0$, a population of nuclei precessing at the Larmor frequency equal to f would align at an angle $\theta$ relative to the $B_0$ direction. The precessing of the aligned nuclei about the $B_0$ vector produces a changing magnetic flux that induces a current in the RF antenna coil. This is the mechanism through which the NMR signal of the sample is observed. The nutation angle $\theta$ is given by $\theta = \gamma B_1 t_p$, where $\gamma$ is the gyromagnetic ratio, $B_1$ is the linearly polarized oscillating field strength, and $t_p$ is the duration of the pulse. The Larmor frequency $\omega$ is given by, $$\omega = (\gamma B_0), \tag{1}$$

where $\gamma$ is the gyromagnetic ratio of the nuclear species of interest, and $B_0$ is the strength of the static magnetic field.

For hydrogen nuclei, the gyromagnetic ratio ($\gamma/2\pi$) is typically 4258 Hz/Gauss.

The nutation is a complicated "spiral" movement of the macroscopic magnetization of the nuclei away from the z-axis toward the x-y plane of the fixed laboratory frame. In a rotating reference coordinate system that rotates about the z-axis of the fixed laboratory frame at an angular frequency $\omega$ (which is commonly referred to as the rotating coordinate frame or rotating frame), this process is a simple rotation of the macroscopic magnetization of the nuclei about the axis of the oscillating magnetic field $B_1$. The nutation angle is a function of both the magnitude and duration of the radio frequency signal passed through the RF antenna coil. The radio frequency signal where the axis (direction) of the oscillating magnetic field $B_1$ is aligned with the positive x direction of the laboratory frame and the nutation is 90 degrees such that macroscopic magnetization of the nuclei is aligned in the positive y direction of the laboratory frame is referred to as a "90 degree pulse in the x direction" or "90 x pulse." The radio frequency signal where the axis of the oscillating magnetic field $B_1$ is aligned with the positive x direction of the laboratory frame and the nutation is 180 degrees such that macroscopic magnetization of the nuclei is aligned in the negative z direction of the laboratory frame is referred to as "a 180 degree pulse in the x direction" or "180 x pulse." The radio frequency signal where the axis of the oscillating magnetic field $B_1$ is aligned with the positive y direction of the laboratory frame and the nutation is 90 degrees such that macroscopic magnetization of the nuclei is aligned in the negative x direction of the laboratory frame is referred to as "a 90 degree pulse in the y direction" or "90 y pulse." When two or more pulses are applied back-to-back, depending on the phase of the pulses of the sequence, a composite nutation results.

Several different effects contribute to the observed NMR signal that follows such nutation. The first of these in the free induction decay (FID) caused by the inhomogeneity of the magnetic field, which causes the individual precessing vectors to grow out of phase. The other two are commonly referred to as spin-lattice interaction and spin-spin interaction.

Spin-lattice interaction is a measure of how quickly the system "resets" back into the low-energy configuration (i.e., thermal equilibrium) with the nuclei aligned with the static $B_0$ magnetic field. The spin-lattice interaction is characterized by a spin-lattice relaxation time $T_1$. For example, a standard technique for measuring the spin-lattice relaxation time $T_1$ (referred to as inversion recovery) utilizes an RF pulse sequence that involves the application of a 180 x pulse followed by a 90 x pulse after a time period $t_1$. The 180 x pulse aligns the magnetization to the negative z direction. The time period $t_1$ allows for partial relaxation of the longitudinal (negative z direction) magnetization toward the equilibrium state. This is commonly referred to as longitudinal relaxation. The 90 x pulse projects the partially relaxed magnetization onto the y-axis. The amplitude of the FID after the 90 x pulse decays according to an exponential function characterized by the spin-lattice relaxation time $T_1$. Another standard technique for measuring the spin-lattice relaxation time $T_1$ (referred to as saturation recovery) utilizes an RF pulse sequence that involves the application of a first 90 x pulse followed by a second 90 x pulse after a time period $t_1$. The amplitude of the FID after the second 90 x pulse decays according to an exponential function characterized by the spin-lattice relaxation time $T_1$.

Spin-spin interaction is a measure of how quickly the transverse precessing of the nuclei decay. The spin-spin interaction is characterized by a spin-spin relaxation time $T_2$. For example, at the end of a 90 x pulse, all the spins can be pointed in a common direction perpendicular, or transverse, to the direction the static $B_0$ magnetic field, and they all precess at the Larmor frequency. However, because of small fluctuations in the static field induced by other spins, paramagnetic impurities and the inhomogeneity of the static $B_0$ magnetic field, the spins precess at slightly different frequencies, and the transverse magnetization dephases over time. This is commonly referred to as traverse relaxation. The relaxation (dephasing) of the transverse magnetization decays with a time constant referred to as the spin-spin relaxation time $T_2$. A standard technique for measuring the spin-spin relaxation time $T_2$ utilizes an RF pulse sequence known as the CPMG (Carr-Purcell-Meiboom-Gill) sequence. As is well known, a 90 x pulse is applied to cause the spins to start precessing in the transverse x-y plane. After an initial delay of $\tau$, an initial 180 x pulse is applied to cause the spins, which are dephasing in the transverse x-y plane, to reverse direction and to refocus and subsequently cause an initial spin echo to appear after a delay of $\tau$ (or $2\tau$ from the 90 x pulse). A second 180 x refocusing pulse can be applied to cause a second spin echo to appear. Thereafter, a series of 180 x pulses separated by a short time delay ($2\tau$) are applied to repeatedly reverse the spins, thereby causing a series of "spin echoes" to appear. An echo time $t_E$ of $2\tau$ is indicative of the spacing between echoes and the spacing between the refocusing pulses. The magnitude of the stimulated spin echoes decreases with time due to molecular relaxation and diffusion. The decay of such spin echo magnitudes over time follows an exponential function characterized by the spin-spin relaxation time $T_2$.

In a uniform static magnetic field, each spin will experience the same magnetic field strength regardless of its position within the static field, and diffusion will not contribute to the observed spin-spin relaxation time $T_2$. However, in the magnetic field gradient of the inhomogeneous static magnetic field $B_0$, each spin will experience different magnetic field strengths as it diffuses through the static field. The Larmor frequencies of the diffusing spins become time dependent, and the 180-degree pulses cannot refocus the spins completely, leading to an additional decay. This additional decay contributes to the observed spin-spin relaxation time $T_2$ and is dependent on the diffusion coefficient D of the fluid. As the diffusion coefficient D provides an indication of fluid type, measurement of the diffusion effects on observed spin-spin relaxation time $T_2$ can be used as the basis for determining properties of the sample of interest (such as fluid type).

Figure 2:
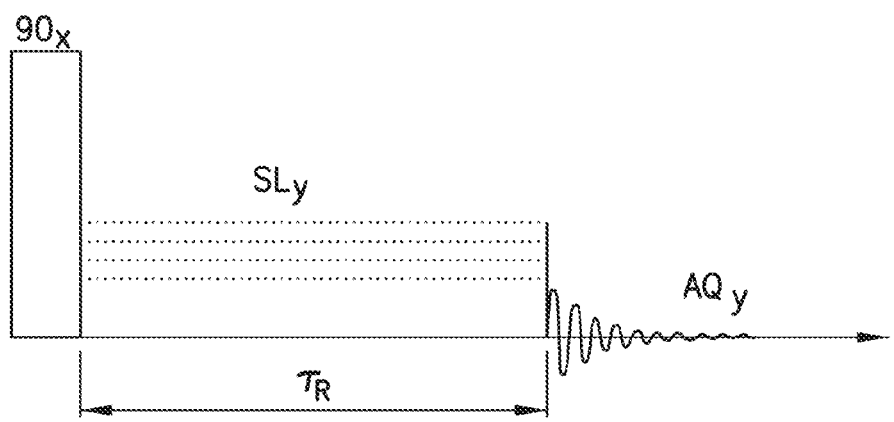
FIG. 2 is a schematic diagram illustrating a prior art NMR pulse sequence used to obtain the relaxation parameter $T_{1\rho}$ for one or more particular frequencies.
Figure 1B:
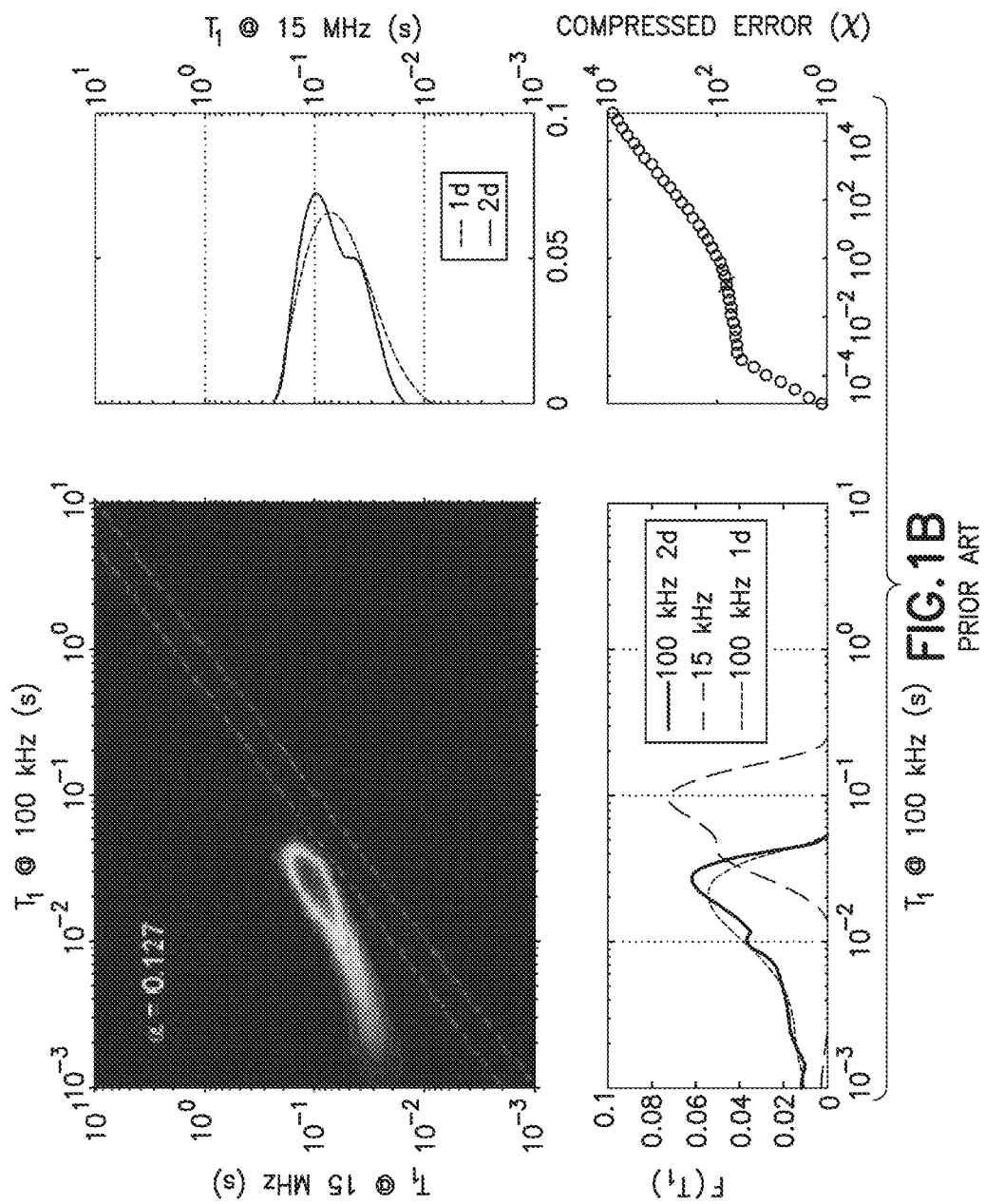
FIG. 1B is an illustration of the $T_1$-$T_1$ correlation distribution obtained with the pulse sequence of FIG. 1A on a heavy crude oil sample.

The spin-lattice interaction in the rotating frame is an alternative method to study the relaxation behavior as a function of frequency. Such rotating frame spin-lattice interaction is characterized by a relaxation time $T_{1\rho}$. As described above, a standard technique for measuring the relaxation time $T_{1\rho}$ involves the application of a 90 degree pulse in the x direction followed by the spin locking pulse in the y direction as shown in FIG. 2. Appropriate phase cycling can then be carried out as known in the art. The duration of the spin locking pulse is varied systematically to cover the whole range of expected relaxation times and applied to the transverse magnetization of the nuclei of the sample. While the spin locking pulse is being applied, the magnetization of the nuclei of the sample is polarized along the field direction of the spin locking pulse in the rotating frame. The magnetization of the nuclei is therefore locked to the axis of the applied spin locking pulse in much the same way that an equilibrium magnetization vector is locked to the static magnetic field $B_0$. The spins that are locked by the field of the spin locking pulse will decay in rotating frame according to the spin-spin relaxation time $T_{1\rho}$. The magnitude of the spin lock pulse (and thus the frequency $\omega_1$ of the spin lock field) can be varied over multiple suites of NMR measurements as represents by the dotted lines in FIG. 2.

In one embodiment, the dependence of the $T_{1\rho}$ decays on the duration of the spin locking pulses can be inverted to obtain the one dimensional $T_{1\rho}$ distributions. The one-dimensional $T_{1\rho}$ distributions can then be stacked on top of each other as a function of the $\omega_1$ frequency (or spin lock pulse amplitude) to provide information about the dispersion of different constituents of the distribution. A typical outcome of such processing is shown in the FIG. 3, where the distribution of relaxation times is shown to vary with the spin lock frequency ($\omega_1$), defining the so called "dispersion of distributions." For a simple fluid such as water, the distributions would be narrow (delta functions in the limit of infinite measurement resolution) and straight vertical in the relevant frequency range. When there is a distribution at each frequency, it indicates that multiple molecular species are present. The dispersion is indicative of the interactions between the different species as well as the dynamics of large complex molecules as are present, for instance, in heavy crude oils. The range of 1 kHz-100 kHz is a typical range available with commercial spectrometers.

The NMR measurements as described above can be adapted to perform multidimensional NMR experiments that utilize RF pulse sequences of different shapes, frequencies and durations to extract multidimensional distributions for many different types of information about the sample. As the experiment is repeated, the pulse sequence is systematically varied. The multidimensional NMR experiments can employ multidimensional correlations of relaxation and diffusion properties like $T_{1\rho}$-$T_{1\rho}$, $T_{1\rho}$-$T_2$ $T_{1\rho}$-$T_1$-$T_2$. Specifically, the observed relaxation parameters are determined by appropriate time correlation functions as applied to the spectral density of the NMR signal and evaluated at certain frequencies, thus certain magnetic fields.

Figure 4:
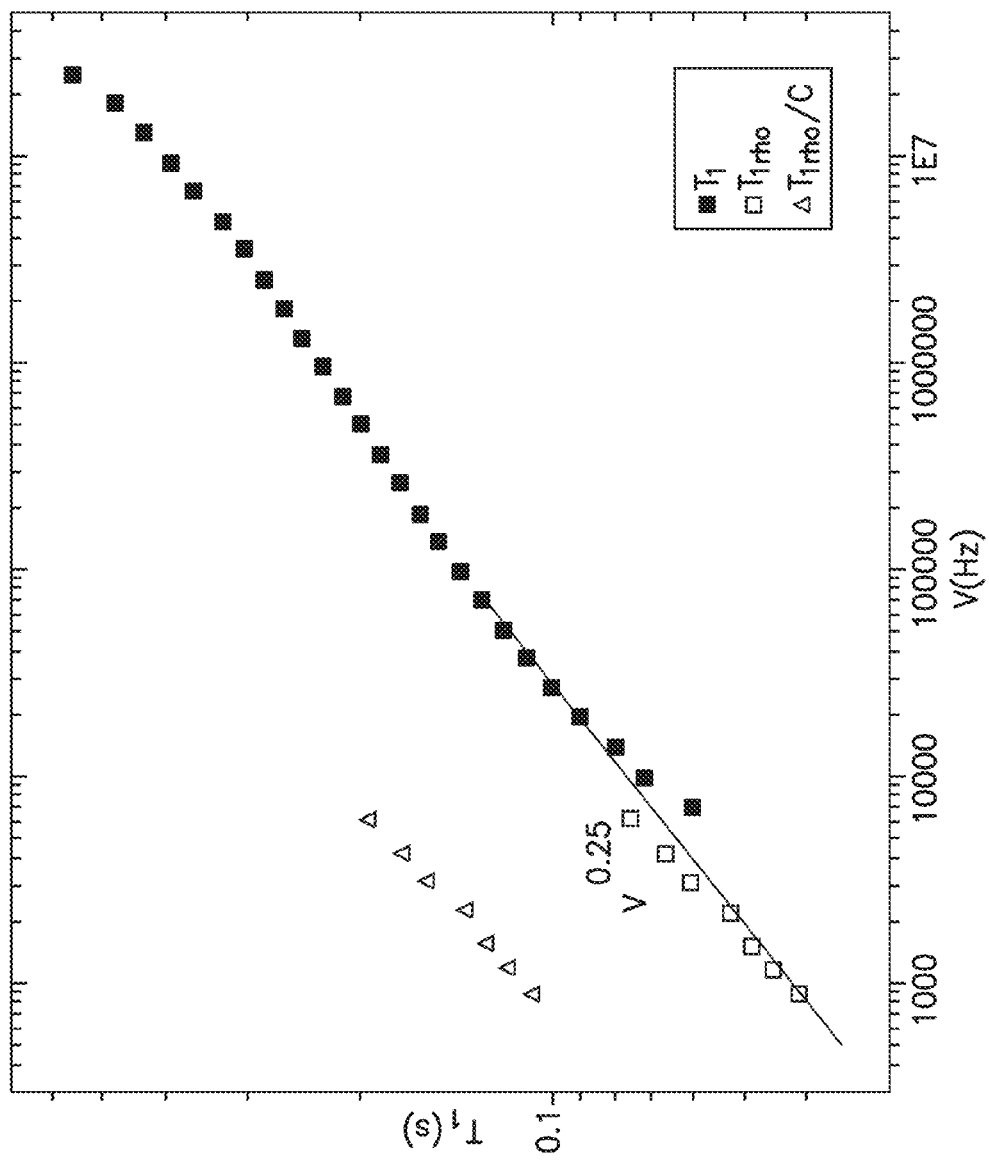
FIG. 4 is a plot illustrating the dispersion of spin-lattice relaxation times $T_1$ and $T_{1\rho}/c$ (where c is a numerical constant) of Poly-dimethysiloxane.

As an example, the spin-lattice relaxation dispersion of poly-dimethysiloxane is shown in FIG. 4. The $T_1$ data from the field cycling relaxation experiment extending from 10 KHz to 40 MHz is plotted alongside the $T_{1\rho}$/c (where c is a numerical constant) data measured with a superconducting magnet ($\omega_0$=400 MHz) from ~1 KHz to ~20 KHz. The frequency dependence of $T_1$ with $\omega_0$ is shown to be similar to that of $T_{1\rho}$ to $\omega_1$ thus showing one potential usefulness of such applications.

In some cases, the spin-lattice relaxation time $T_1$ can be correlated to the spectral density of the NMR signal according to the following:

$$\frac{1}{T_1} = \left(\frac{\mu_0}{4\pi}\right)^2 \frac{3}{10 r^6} \gamma^4 \hbar^2 \left[\frac{\tau_c}{1+\omega^2 \tau_c^2} + \frac{4\tau_c}{1+4\omega^2 \tau_c^2}\right] \quad (1)$$

where $\mu_0$ is the permittivity of free space, $\omega$ is the Larmor frequency, $\gamma$ is the proton gyromagnetic ratio, r is the internuclear distance, h is h/2$\pi$ where h is Planck's constant, and $r_c$ is the correlation time.

In some cases, the spin-spin relaxation time $T_2$ can be correlated to the spectral density of the NMR signal according to the following:

$$\frac{1}{T_2} = \left(\frac{\mu_0}{4\pi}\right)^2 \frac{3}{20 r^6} \gamma^4 \hbar^2 \left[3\tau_c + \frac{5\tau_c}{1+\omega^2 \tau_c^2} + \frac{2\tau_c}{1+4\omega^2 \tau_c^2}\right] \quad (2)$$

Note the spin-lattice relaxation time $T_1$ is sensitive to motions at the Larmor frequency of the measurement. The spin-spin relaxation time $T_2$ is mainly sensitive to the low frequencies with a weak dependence on the Larmor frequency because the first term in the spectral density dominates in Eqn. (2). Thus a multidimensional NMR experiment which measures the correlation between $T_1$ and $T_2$ relaxation times would provide information on the dispersion between the Larmor frequency and 'zero' or low frequency. But as the Larmor frequency of the magnet is fixed for permanent and superconducting magnets, the correlations are useful for a limited frequency range. In addition, the $T_2$ relaxation time can be affected by motions in the time scale of the echo times used for its measurement, thus making the interpretation of the dispersion complicated. In such cases the first term in the spectral density for $T_2$ can be modeled as $3\tau_c/T_E$, where $T_E$ is the echo time.

In some cases, the spin-lattice relaxation time $T_{1\rho}$ can be correlated to the spectral density of the NMR signal according to the following:

$$\frac{1}{T_{1\rho}} = \left(\frac{\mu_0}{4\pi}\right)^2 \frac{3}{20 r^6} \gamma^4 \hbar^2 \left[\frac{3\tau_c}{1+4\omega_1^2 \tau_c^2} + \frac{5\tau_c}{1+\omega^2 \tau_c^2} + \frac{2\tau_c}{1+4\omega^2 \tau_c^2}\right] \quad (3)$$

where $\omega_1$ is dictated by the magnitude (strength) of the spin lock field.

Note that Eqn. (3) has a form similar to Eqn. (2), but the first term has a clear dependence on $\omega_1$. As the absolute values of $T_{1\rho}$ are dominated by the first term in the spectral density (as $\omega_1 \ll \omega$), $T_{1\rho}$ as a function of $\omega_1$ can be obtained.

Note that other appropriate correlation functions can be used as well for each of the relaxation times, depending on the dynamics studied.

Figure 5A:
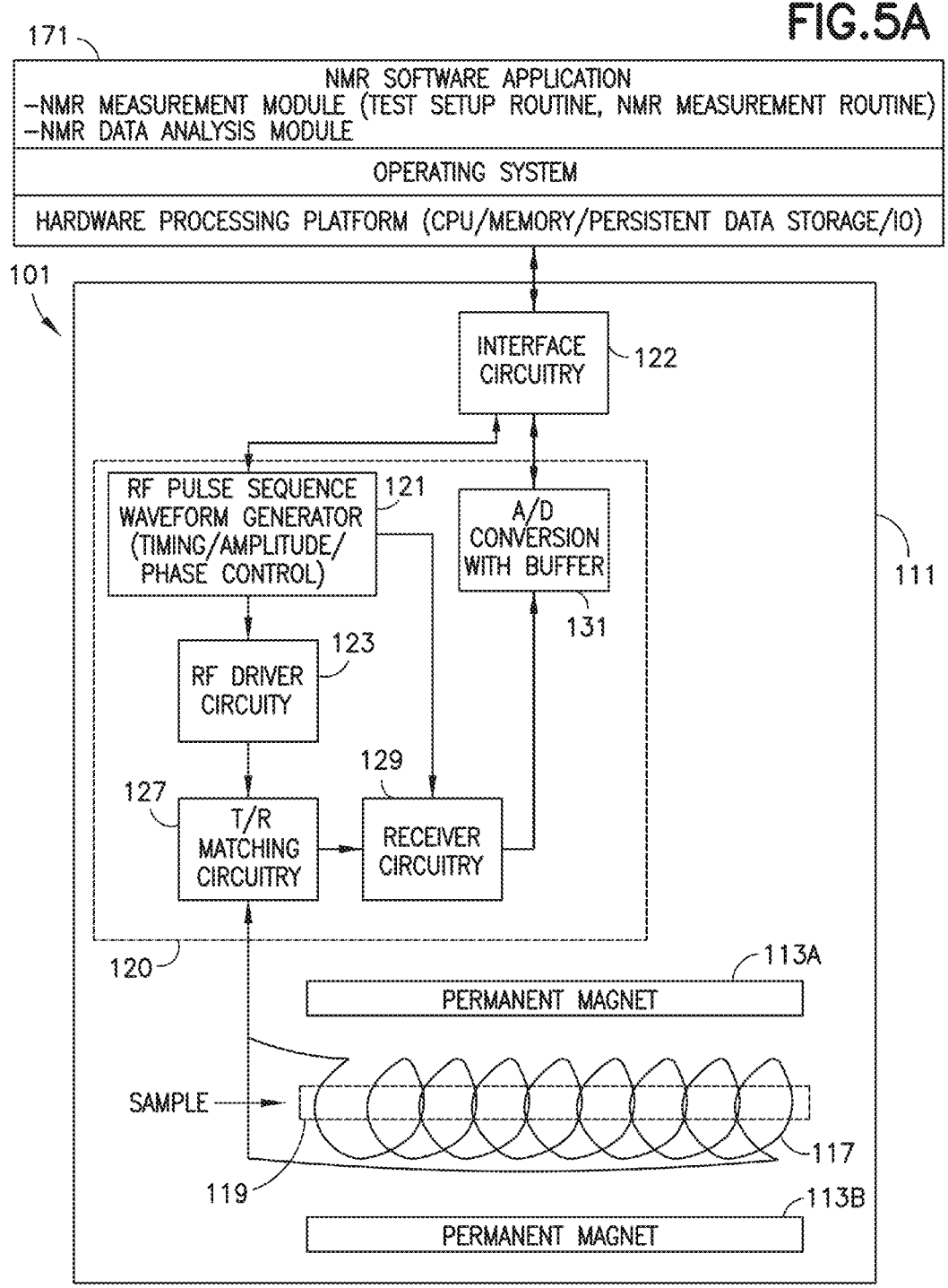
FIG. 5A is a schematic diagram of an NMR spectrometer which can be used in practicing embodiments of the present application.
Figure 5B:
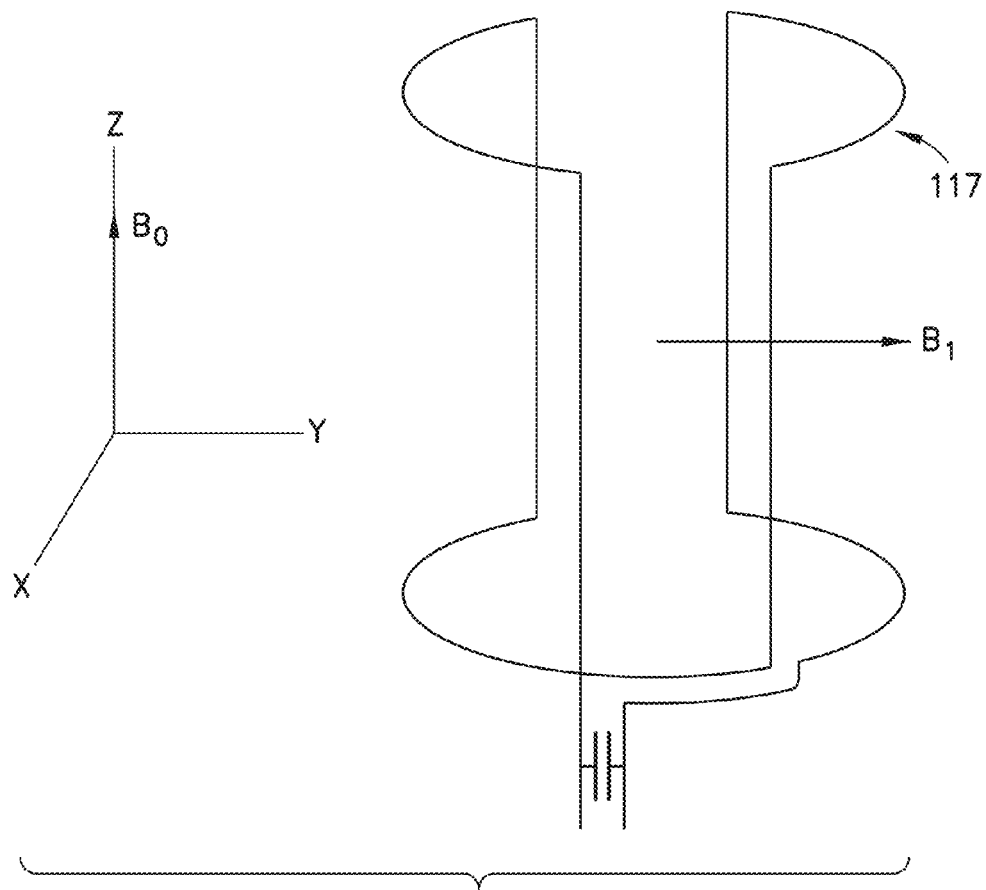
FIG. 5B is a schematic diagram of a saddle coil and reference (laboratory) coordinate system for use in the NMR spectrometer of FIG. 5A.

FIG. 5A shows an NMR spectrometer 101 for carrying out NMR measurement and analysis of a sample in accordance with an embodiment of the present application. The NMR spectrometer 101 includes an NMR instrument housing 111 that houses a magnet array (e.g., permanent magnets 113A, 113B) and an RF antenna 117 encompassing a sample volume 119. A sample of interest is selected for testing and placed in the sample volume 119. The sample of interest can be contained within a sample holder that is placed in the sample volume 119. A conveyor or other drive mechanism can convey the formation sample of interest through the sample volume 119 as is well known. The magnet array 113A, 113B produces a generally homogeneous static magnetic field $B_0$ in the sample volume 119. The strength of the static magnetic field $B_0$ can vary depending upon the application. The RF antenna 117 transmits pulses of an oscillating magnetic field $B_1$ across the sample volume 119. The magnetic moment of the magnetic field $B_1$ is substantially perpendicular to the static magnetic field $B_0$. The orientation of the magnetic fields $B_0$ and $B_1$ are referenced in a fixed Cartesian coordinate system (commonly referred to as the laboratory coordinate frame or laboratory frame), where the static magnetic field $B_0$ lies along the z-axis and the magnetic moment of the magnetic field $B_1$ lies in the x-y plane. An example of a saddle-type RF antenna 117 referenced in a fixed Cartesian coordinate system is shown in FIG. 5B.

The NMR instrument housing 111 also contains electronic circuitry 120 that interfaces to the RF antenna 117 to carry out NMR measurements on the sample of interest in the sample volume 119. The electronic circuitry 120 operates in three modes: excitation mode, damping mode, and receiving mode. In the excitation mode, the RF antenna 117 is excited such that it radiates a pulse of an oscillating magnetic field $B_1$ across the sample volume 119. The pulse of oscillating magnetic field $B_1$ resonates nuclear spins in the sample of interest disposed in the sample volume 119. In the receive mode, the RF antenna 117 receives oscillating magnetic signals of the nuclear spin precession radiating from the sample of interest disposed in the sample volume 119. The damping mode is carried out between the excitation mode and receive mode in order to limit ringing of the RF antenna 117 at the end of the pulse of the oscillating magnetic field $B_1$.

In one embodiment, the electronic circuitry 120 includes a circuit block 121 for generating RF pulse sequence waveforms that excite the pulses of oscillating magnetic field $B_1$ across the sample volume 119. The parameters of the RF pulse sequence waveforms may be controlled by control signals supplied to circuit block 121 from computer 171 via interface block 122. The RF pulse sequence waveforms generated by circuit block 121 are supplied to an RF drive circuitry 123 that amplifies the RF pulse sequence waveform to suitable power levels for supply to the RF antenna 117 in the excitation mode such that the RF antenna 117 radiates pulses of oscillating magnetic field $B_1$ oscillating at the Larmor frequency of the nucleus of interest.

On one embodiment, the T/R Matching circuitry 127 provides an impedance that matches the input impedance of the RF antenna 117 in the excitation mode in order maximize power transmission to the RF antenna 117, and also provides an impedance that matches the input impedance of the receiver circuitry 129 in the receive mode in order to minimize noise. The T/R Matching circuitry 127 also provides impedance that dampens the RF antenna 117 in the damping mode in order to limit ringing of the RF antenna 117 at the end of the pulse of the oscillating magnetic field $B_1$. In the receive mode, the receiver circuitry 129 amplifies the signals captured by the RF antenna 117 and supplied by the T/R Matching circuitry 127, and utilizes a reference signal supplied by the circuit block 121 (this reference signal corresponds to the frequency of interest) and the amplified signal to obtain a measured NMR resonance signal at the frequency of interest from the sample volume 119. The receiver circuitry 129 can employ a superheterodyne receiver architecture, a homodyne receiver architecture or other suitable design. The measured NMR resonance signal is output to an analog-to-digital converter 131 for sampling and conversion into digital form. The digital data is buffered and forwarded to the computer 171 via interface block 122 for further use and analysis.

The computer 171 includes a hardware processing platform that includes at least one central processing unit, memory, persistent data storage (e.g., a hard disk drive or optical disk), I/O functionality, and other functionality as is well known in the data processing arts. The persistent data storage stores an operating system and a software application (a programmed sequence of instructions) that are both loaded into memory for execution by the central processing unit(s) of the platform as is well known. In an embodiment, the computer 171 is realized by a commercially available workstation that interfaces to the NMR instrument housing 111 by a suitable interface, such as a USB or 1394 data link. The software application embodies an NMR Measurement module and an NMR Data Analysis module that carry out the NMR measurement and analysis of the sample of interest. The NMR Measurement module performs NMR measurements on the sample of interest. The NMR measurements are derived from operation of a test setup routine and NMR measurement routine.

The test setup routine interfaces with the waveform generator circuit block 121 to supply the parameters (e.g., pulse duration, amplitude and timing parameters) for programming the desired pulse sequence of oscillating magnetic field $B_1$ to be emitted by the RF antenna 117 for a suite of NMR measurements (FIG. 5B).

The NMR measurement routine triggers the electronic circuitry block 120 to radiate the sample volume 119 with the desired pulse sequence of oscillating magnetic field $B_1$ and measures and records the NMR resonance signals that result from the suite of NMR measurements.

The NMR Data Analysis module processes the NMR data recorded from one or more suites of NMR measurements carried out by the NMR Measurement module to characterize NMR-related parameters as well as other properties of the sample of interest, and stores the results of NMR data analysis for the sample of interest. Such stored results can be output (for example, presented to a user on a display screen).

The NMR experiments can also be carried out with NMR logging tools which generally use permanent magnets and have correspondingly different electronics for the applications of RF pulses and data acquisition and analysis as known in the art.

Figure 6:
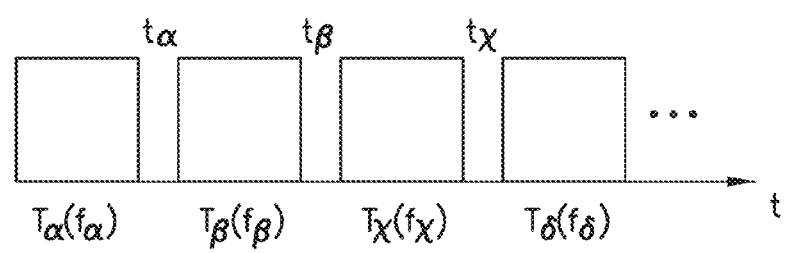
FIG. 6 is a schematic diagram illustrating a second embodiment of a generalized NMR pulse sequence which can be used by the NMR spectrometer of FIG. 5A in accordance with the present application.

FIG. 6 shows a generalized pulse sequence of oscillating magnetic field $B_1$ that is emitted by the RF antenna 117 of the spectrometer 101 in a suite of NMR measurements carried out by the NMR Measurement module according to the present application. The pulse sequence begins with a preparation phase where the spins are generally sufficiently close to thermal equilibrium (or in some steady state condition) and then a pulse or a series of pulses (such as 90 x pulse or 180 x pulse) is provided to produce a desired orientation of the magnetization (e.g., aligned to the positive y direction for a 90 x pulse or aligned to the negative z-direction for a 180 x pulse). An evolution phase follows the preparation phase. The evolution phase includes a sequence of one or more pulses (or measurement segments) that are suitable for measuring particular relaxation parameters of which at least one is $T_{1\rho}$ and others such as D, $T_1$ and $T_2$. Four measurement segments are shown as $T_\alpha(f_\alpha)$, $T_\beta(f_\beta)$, $T_\chi(f_\chi)$, $T_\delta(f_\delta)$ as an example. The frequencies of the measurement segments can vary with respect to one another for the suite of NMR measurements. Thus, $f_\alpha$, $f_\beta$, $f_\chi$ and $f_\delta$ can be different from one another for the suite of NMR measurements. Intervals (labeled $\tau_\alpha$, $\tau_\beta$, $\tau_\chi$, $\tau_\delta$) can follow the corresponding measurement segment if desired and could have values 0 and above. At least one of the measurement segments is realized by a spin lock pulse that is suitable for measuring $T_{1\rho}$ at a particular frequency (defined by the magnitude of the spin lock field). The other measurement segments can be suitable for measuring $T_{1\rho}$ at a different frequency (defined by the magnitude of the spin lock field of a spin lock pulse) and/or can be suitable for measuring $T_1$ at the Larmor frequency (such as 90 x pulse after a predefined wait time following the preparation phase) and/or can be suitable for measuring $T_2$ (such as CPMG echo excitation sequence with an echo times $t_E$ corresponding to the desired frequency or multiple segments with as CPMG echo excitation sequences having different echo times $t_E$) and/or diffusion. An acquisition phase follows (or is interposed within) the evolution phase to detect the evolved transverse magnetization. The detected NMR signal is digitized and stored as NMR data for each pulse sequence in the suite of NMR measurements. Such NMR data is processed by inversion (such as a multidimensional inverse Laplace transformation) that derives the distribution functions in multiple dimensions which are the relaxation or diffusion parameter dimensions. Such distribution functions of which $T_{1\rho}$ at a particular chosen frequency is one, can be analyzed to determine properties of the sample of interest. This enables the study of correlations between relaxation distribution of $T_{1\rho}$ at a predefined frequency with dynamics which are sensitive to different frequencies, like with $T_1$ at the larmor frequency, $T_2$ which is sensitive to the echo time and low frequencies, diffusion and even $T_{1\rho}$ at other frequencies. For example, the different relaxation and/or diffusion parameters of the multidimensional distribution functions can be plotted along different axes to understand the correlations between them for the sample of interest.

The different measurement segments (e.g., measurement segment for $T_{1\rho}$ at a particular frequency, measurement segment for $T_1$ at another frequency, and a measurement segment for $T_2$ at a different (or same) frequency) may be combined in an arbitrary fashion to provide similar type of information or to weight different regimes or interactions differently as appropriate in a given application. The inversion kernels can be modified appropriately to reflect the exact sequence at hand. This can be done in many ways; for example by a straightforward generalization of the 1D and 2D Laplace inversions which are well-known to those skilled in the art. Appropriate phase cycling can be carried out.

Note that the evolution phase of the NMR experiments of FIG. 6 can employ other pulse sequences well known in the field of NMR. For example, such pulse sequences can be designed to produce correlations between chemical shifts (referred to as chemical shift resolved NMR) such that the relaxation dispersion correlations of different chemical constituents can be separately visualized. In another example, the sequences and classes of sequences described herein (combinations of $T_{1\rho}$, $T_1$ and $T_2$, at different frequencies) can be further modulated by the additional relaxation due to diffusion in a magnetic field gradient. As is well-known, larger molecular structures diffuse more slowly than small ones, and a more viscous medium slows the diffusion of all particles. Diffusion weighting is a standard technique in the world of NMR, common for example in medical imaging applications. In these applications, a diffusion weighting segment can be inserted at any point between the different relaxation encoding measurement segments. Thus the general sequence of multi-frequency measurement blocks $T_\alpha(f_\alpha)-\tau_\alpha-T_\beta(f_\beta)-\tau_\beta-T_c(f_\chi)-\tau_\chi-T_\delta(f_\delta)-$ . . . can be further generalized such that now each segment block can also represent a diffusion-encoding stage. The inversion kernel can be adapted to reflect the diffusion encoding stage.

Figure 3:
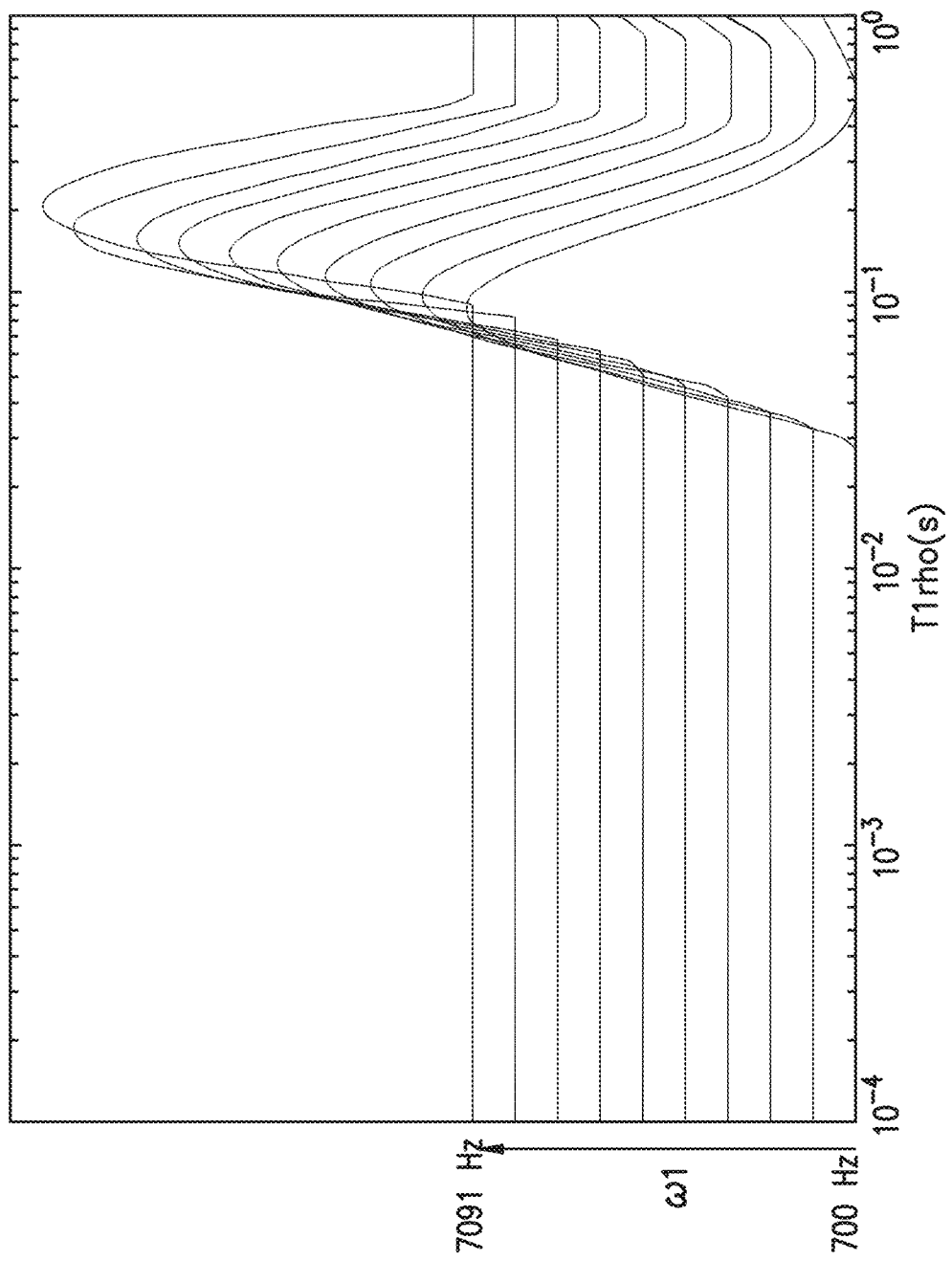
FIG. 3 is a first embodiment of a stacked plot of one-dimensional distributions of the relaxation parameter $T_{1\rho}$ (x-axis) obtained by inverting the $T_{1\rho}$ decays for a number of different frequencies (y-axis) and plotted to show the correlations between the relaxation distributions at various frequencies.

The NMR signals acquired after $T_{1\rho}$ experiments at different frequencies (spin lock strengths) can be individually inverted by a transformation like a 1D inverse Laplace transformation, and the data stacked on top of each other to understand the correlations between different parts of the relaxation distributions as shown in FIG. 3. The 1D distribution functions can be stored for display and/or printing for analysis of the sample of interest. Inspection for correlations from different parts of the distributions would help provide information about the system.

Figure 7:
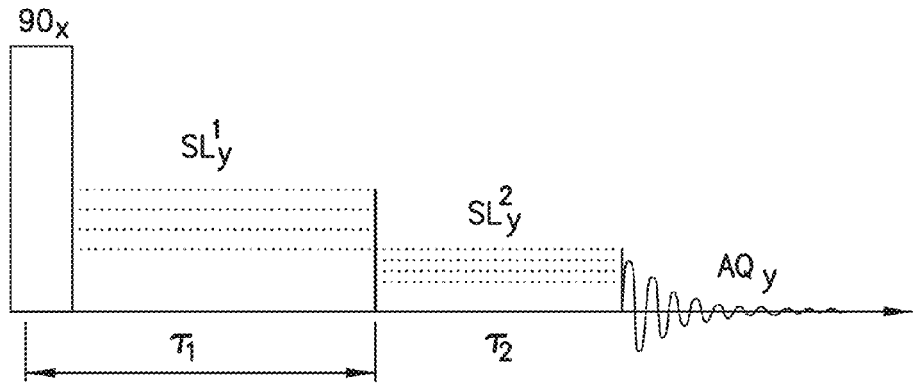
FIG. 7 is a schematic diagram illustrating a third embodiment of a NMR pulse sequence which can be used by the NMR spectrometer of FIG. 5A in accordance with the present application.

In a first embodiment, the respective pulse sequences of oscillating magnetic field $B_1$ that are emitted by the RF antenna 117 of the spectrometer 101 in a suite of NMR measurements carried out by the NMR Measurement module following the pulse sequence shown in FIG. 7, which includes a 90 degree pulse in the x direction (labeled 90$_x$) followed by a first spin lock pulse in the y direction (labeled $SL^1_y$) of a particular magnitude for a duration $\tau_1$ and then a second spin lock pulse in the y direction (labeled $SL^2_y$) of a different magnitude for a duration $\tau_2$. The magnitudes of the respective spin lock pulses dictates the frequencies $\omega_1$ and $\omega_2$ of the corresponding spin lock fields. The duration $\tau_2$ can be varied for different values of $\tau_1$ (or vice versa) over the suite of NMR measurements. The NMR resonance signal (labeled $AQ_y$) that follows the second spin lock pulse is digitized and stored as NMR data for each pulse sequence in the suite of NMR measurements. The NMR Data Analysis module processes such NMR data by inversion to generate the two dimensional $T_{1\rho}$ relaxation distribution functions (the first corresponding to $T_{1\rho}$ at frequency $\omega_1$, and the second corresponding to $T_{1\rho}$ at frequency $\omega_2$). The inversion can utilize 2D-Inverse Laplace Transformation or other methods. Such distribution functions can be analyzed to determine properties of the sample of interest. For example, a two-dimensional $T_{1\rho}-T_{1\rho}$ distribution plot for the given frequency pair $\omega_1$ and $\omega_2$ can be derived from the two distribution functions and stored for display and/or printing for analysis of the sample of interest. Inspection for correlations from different parts of the distributions would help provide information about the system.

In alternate embodiments, the magnitudes of the spin lock pulses $SL^1_y$ and $SL^2_y$ can be varied over different suites of NMR measurements as represented by the dotted lines in FIG. 7 in order to vary the frequencies $\omega_1$ and $\omega_2$ of the corresponding spin lock fields. Correlations between the two-dimensional $T_{1\rho}-T_{1\rho}$ relaxation distributions at various different frequencies can then be analyzed to determine properties of the sample of interest.

Figure 8:
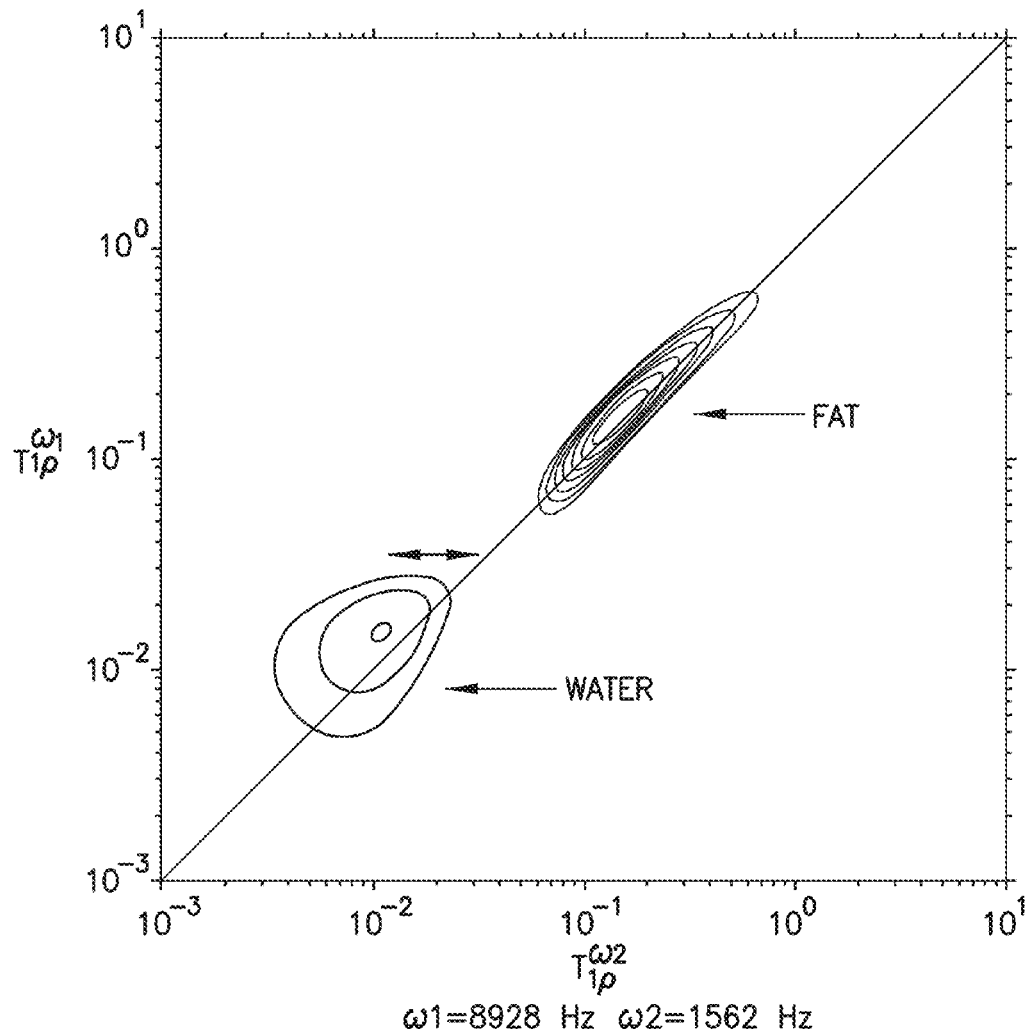
FIG. 8 is a two-dimensional $T_{1\rho}$-$T_{1\rho}$ distribution plot of a sample of Gruyere cheese obtained with the pulse sequence of FIG. 7 at a Larmor frequency of 400 MHz and spin lock frequencies of 8928 Hz and 1562 Hz.

FIG. 8 shows a two-dimensional $T_{1\rho}-T_{1\rho}$ distribution plot of a sample of Gruyere cheese obtained with the pulse sequence of FIG. 7 at a Larmor frequency of 400 MHz. The first spin lock frequency $\omega_1$ is at 8928 Hz while the second spin lock frequency $\omega_2$ is at 1562 Hz. The two-dimensional $T_{1\rho}-T_{1\rho}$ distribution plot shows the correlation in the dispersion between these two frequencies. The motionally averaged fat signal is on the diagonal while the water signal which has a finite dispersion is shown well separated. Therefore both fluid typing and information of the dynamics of the different species is obtained.

Figure 9:
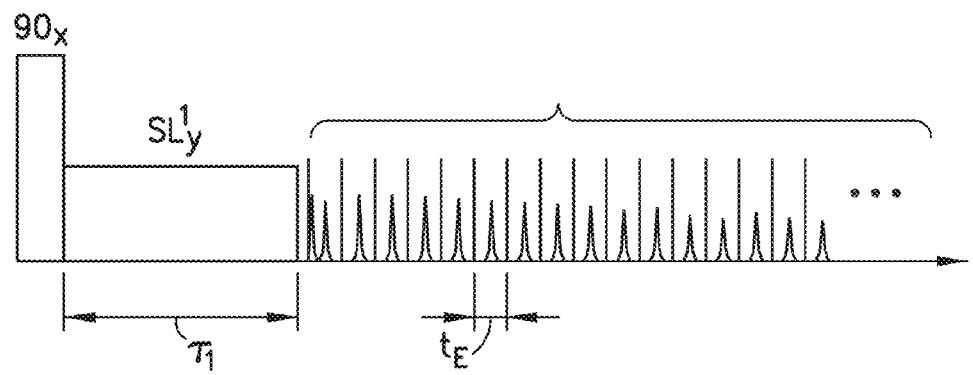
FIG. 9 is a schematic diagram illustrating a fourth embodiment of a NMR pulse sequence which can be used by the NMR spectrometer of FIG. 5A in accordance with the present application.

In a second embodiment, the pulse sequences of oscillating magnetic field $B_1$ that are emitted by the RF antenna 117 of the spectrometer 101 in a suite of NMR measurements carried out by the NMR Measurement module follows the pulse sequence shown in FIG. 9, which includes a 90 degree pulse in the x direction (labeled 90$_x$) followed by a spin lock pulse in the y direction (labeled $SL_y$) of a particular magnitude for a duration $\tau_1$ and then a CPMG echo excitation pulse sequence with a particular echo time $t_E$. Appropriate phase cycling can be carried out. The magnitude of the spin lock pulse $SL_y$ dictates the frequency $\omega_1$ of the corresponding spin lock field. The echo time $t_E$ generally determines the frequency to which the $T_2$ relaxation time is sensitive to. The magnitude of the spin lock pulse and the echo time $t_E$ are both constant (not varied) over the suite of NMR measurements. The duration $\tau_1$ is varied over the suite of NMR measurements. The NMR resonance signal that follows each refocusing pulse of the CPMG echo excitation pulse sequence is digitized and stored as NMR data for each pulse sequence in the suite of NMR measurements. The NMR Data Analysis module processes such NMR data by inversion to generate two dimensional distribution functions (the first corresponding to $T_{1\rho}$ at frequency $\omega_1$, and the second corresponding to $T_2$ generally at the frequency dictated by the echo time $t_E$). The inversion can utilize a 2D-Inverse Laplace Transformation or other methods. Such distribution functions can be analyzed to determine properties of the sample of interest. For example, a two-dimensional $T_{1\rho}-T_2$ distribution plot can be derived from the two distribution functions and stored for display and/or printing for analysis of the sample of interest.

Figure 10:
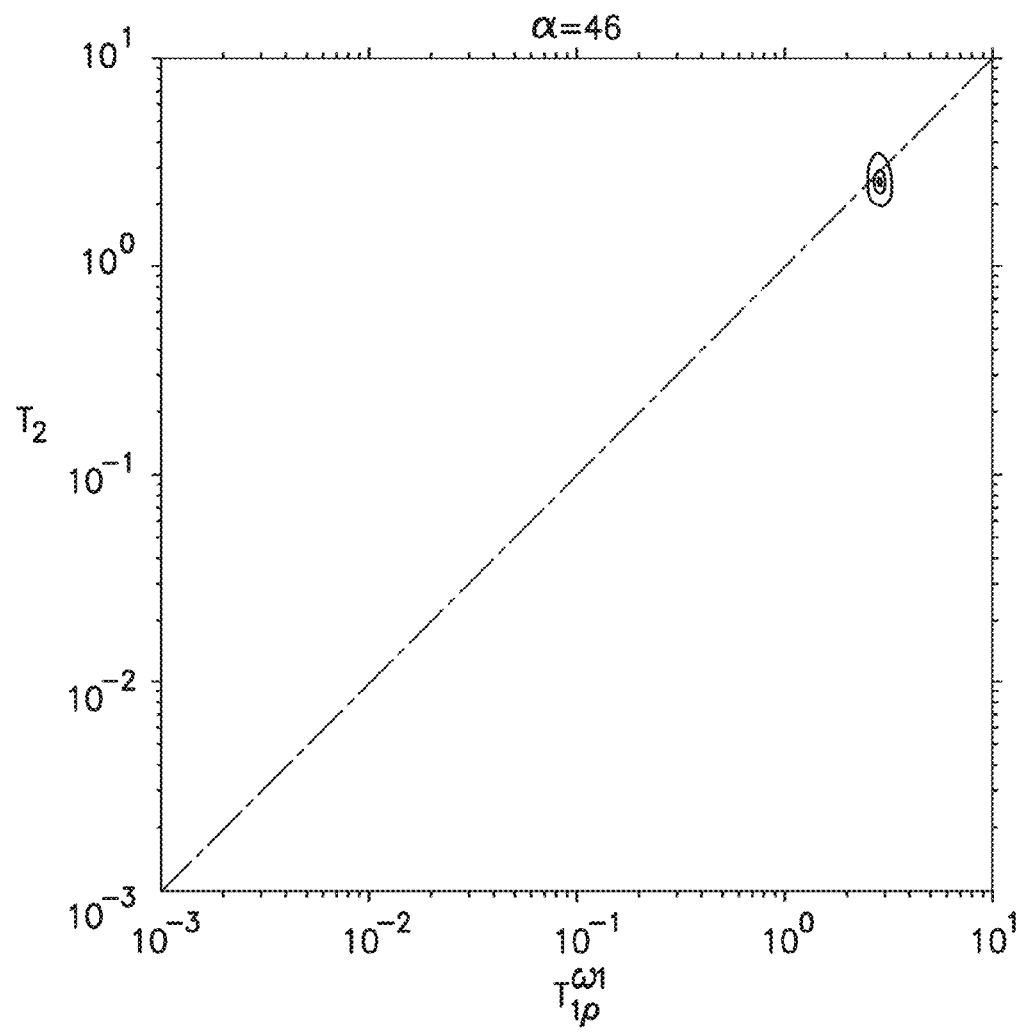
FIG. 10 is a two-dimensional $T_{1\rho}$-$T_2$ distribution plot of a sample of water obtained with the pulse sequence of FIG. 9.

FIG. 10 shows a two-dimensional $T_{1\rho}-T_2$ distribution plot for a sample of water obtained with the pulse sequence of FIG. 9. As water molecules are in the motionally narrowed regime in the frequency window probed, they show no dispersion and the distribution is peaked on the $T_{1\rho}=T_2$ diagonal line.

In alternate embodiments, experiments can be carried out by varying both $\tau_1$ and $t_E$ of the pulse sequence of FIG. 9 over different suites of NMR measurements. Other embodiments include varying the magnitude of the spin lock pulse amplitude in the pulse sequence of FIG. 9 over different suites of NMR measurements.

Figure 11:
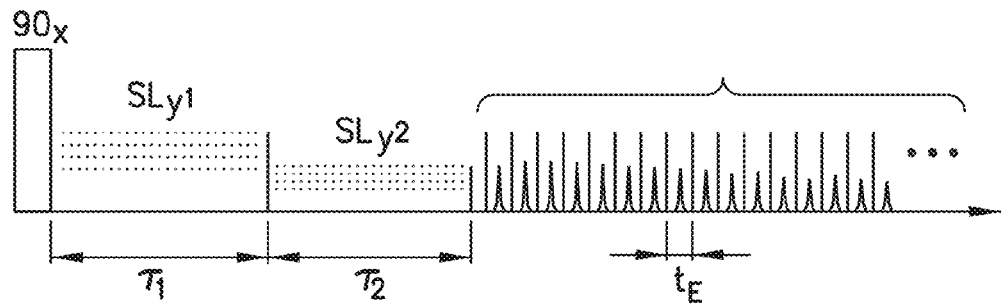
FIG. 11 is a schematic diagram illustrating a fifth embodiment of a NMR pulse sequence which can be used by the NMR spectrometer of FIG. 5A in accordance with the present application.

In a third embodiment, the pulse sequence of oscillating magnetic field $B_1$ that is emitted by the RF antenna 117 of the spectrometer 101 in a suite of NMR measurements carried out by the NMR Measurement module follows the pulse sequence shown in FIG. 11, which includes a 90 degree pulse in the x direction (labeled $90_x$) followed by a first spin lock pulse of a particular magnitude for a duration $\tau_1$ (labeled $SL^1_y$) and then a second spin lock pulse in the y direction (labeled $SL^2_y$) of a particular magnitude for a duration $\tau_2$ and then a CPMG echo excitation pulse sequence with an echo time $t_E$. The magnitude of the respective spin lock pulses $SL^1_y$ and $SL^2_y$ dictates the frequencies $\omega_1$ and $\omega_2$ of the corresponding spin lock fields. The duration $\tau_2$ can be varied for different values of $\tau_1$ (or vice versa) over the suite of NMR measurements. The NMR resonance signal that follows each refocusing pulse of the CPMG echo excitation pulse sequence is digitized and stored as NMR data for each pulse sequence in the suite of NMR measurements. Phase cycling can be carried out for each of the pulses. The NMR Data Analysis module processes such NMR data by inversion to generate multidimensional distribution functions (e.g., the first corresponding to $T_{1\rho}$ at frequency $\omega_1$, the second corresponding to $T_{1\rho}$ at frequency $\omega_2$, and the third corresponding to $T_2$ at the frequency generally dictated by the echo time $t_E$). The inversion can utilize a multidimensional-Inverse Laplace Transformation or other methods. Such distribution functions can be analyzed to determine properties of the sample of interest. For example, a three-dimensional $T_{1\rho}$-$T_{1\rho}$-$T_2$ distribution plot can be derived from the three distribution functions and stored for display and/or printing for analysis of the sample of interest. Other options include plots of 2 selected dimensions to help better understand specific correlations.

In alternate embodiments, the magnitudes of the spin lock pulses $SL^1_y$ and $SL^2_y$ can be varied over different suites of NMR measurements as represents by the dotted lines in FIG. 11 for different frequency pairs of $\omega_1$ and $\omega_2$. The three-dimensional $T_{1\rho}$-$T_{1\rho}$-$T_2$ correlation distributions for the different frequency pairs can be analyzed to determine properties of the sample of interest.

In other embodiments, this experiment can be carried out by varying $t_E$ of the CPMG pulse sequence of FIG. 11 over a suite of NMR measurements.

Figure 12:
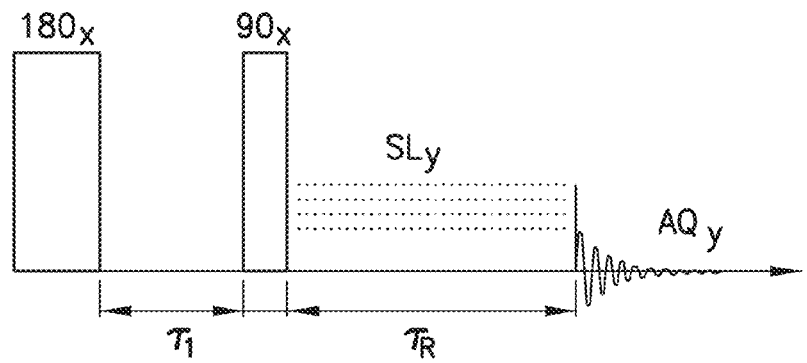
FIG. 12 is a schematic diagram illustrating a sixth embodiment of a NMR pulse sequence which can be used by the NMR spectrometer of FIG. 5A in accordance with the present application.

In a fourth embodiment, the pulse sequence of oscillating magnetic field $B_1$ that is emitted by the RF antenna 117 of the spectrometer 101 in a suite of NMR measurements carried out by the NMR Measurement module follows the pulse sequence shown in FIG. 12, which includes a 180 degree pulse in the x direction (labeled $180_x$) followed by a time delay $\tau_1$ and a 90 degree pulse in the x direction, which is followed by a spin lock pulse in the y direction (labeled $SL_y$) of a particular magnitude for a duration $\tau_R$. Appropriate phase cycling of the pulses can be carried out. The spin lock pulse duration $\tau_R$ can be varied for different values of the time delay $\tau_1$ over the suite of NMR measurements. The magnitude of the spin lock pulse $SL_y$ dictates the frequency $\omega_1$ of the spin lock field. The NMR resonance signal (labeled $AQ_y$) that follows the spin lock pulse is digitized and stored as NMR data for each pulse sequence in the suite of NMR measurements. The NMR Data Analysis module processes such NMR data by inversion to generate two dimensional distribution function (the first corresponding to $T_{1\rho}$ at frequency $\omega_1$, and the second corresponding to $T_1$ at the Larmor frequency). The inversion can utilize a 2D-Inverse Laplace Transformation or other methods. Such distribution functions can be analyzed to determine properties of the sample of interest. For example, a two-dimensional $T_{1\rho}$-$T_1$ distribution plot can be derived from the two distribution functions and stored for display and/or printing for analysis of the sample of interest.

In alternate embodiments, this experiment can be carried out by varying the magnitude of the spin lock pulse $SL_y$ of the pulse sequence of FIG. 12 over a suite of NMR measurements. Such variations in the magnitude of the spin lock pulse $SL_y$ are shown as dotted lines in the pulse sequence of FIG. 12.

In yet other embodiments, experiments that utilize saturation recovery by replacing the initial 180 degree pulse in the x direction (labeled $180_x$) of FIG. 12 with a 90 degree pulse in the x direction. Appropriate phase cycling can be carried out.

Figure 13:
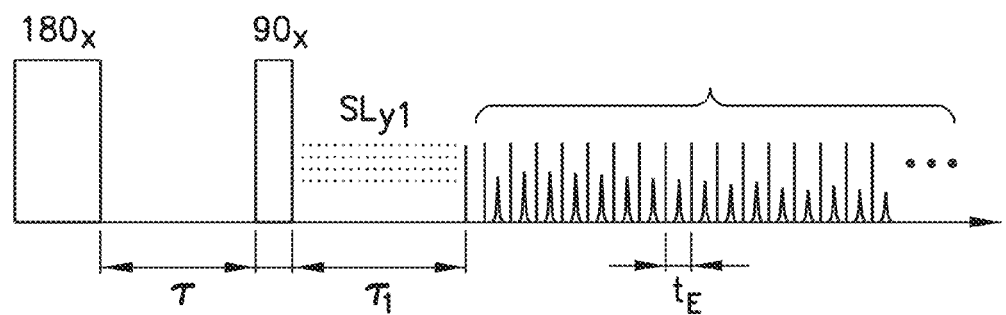
FIG. 13 is a schematic diagram illustrating a seventh embodiment of a NMR pulse sequence which can be used by the NMR spectrometer of FIG. 5A in accordance with the present application.

In a fifth embodiment, the pulse sequence of oscillating magnetic field $B_1$ that is emitted by the RF antenna 117 of the spectrometer 101 in a suite of NMR measurements carried out by the NMR Measurement module follows the pulse sequence shown in FIG. 13, which includes a 180 degree pulse in the x direction (labeled $180_x$) followed by a time delay $\tau$ and a 90 degree pulse, which is followed by a spin lock pulse (labeled $SL_y$) of a particular magnitude for a duration $\tau_R$ and then a CPMG pulse sequence with an echo time $t_E$. Appropriate phase cycling can be carried out. The spin lock pulse duration $\tau_R$ can be varied for different values of the time delay $\tau$ over the suite of NMR measurements. The NMR resonance signal that follows each refocusing pulse of the CPMG echo excitation pulse sequence is digitized and stored as NMR data for each pulse sequence in the suite of NMR measurements. The NMR Data Analysis module processes such NMR data by inversion that derives three dimensional distributions functions (the first corresponding to $T_{1\rho}$ at frequency $\omega_1$, the second corresponding to $T_1$ at the Larmor frequency, and the third corresponding to $T_2$ at the frequency dictated by the echo time $t_E$). The inversion can utilize 3D-Inverse Laplace Transformation or other methods and also obtain just the 2 dimensional distributions if necessary. Such distribution functions can be analyzed to determine properties of the sample of interest. For example, a three-dimensional $T_{1\rho}$-$T_1$-$T_2$ plot can be derived from the three distribution functions and stored for display and/or printing for analysis of the sample of interest.

In alternate embodiments, this experiment can be carried out by varying the magnitude of the spin lock pulse $SL_y$ (for different frequencies $\omega_1$ of the spin lock field) and/or the $t_E$ of the pulse sequence of FIG. 13 over different suites of NMR measurements. Such variations in the magnitude of the spin lock pulse $SL_y$ are shown as dotted lines in the pulse sequence of FIG. 12.

In yet other embodiments, experiments utilizing saturation recovery can replace the initial 180 degree pulse (labeled $180_x$) of FIG. 12 with a 90 degree pulse.

Figure 14:
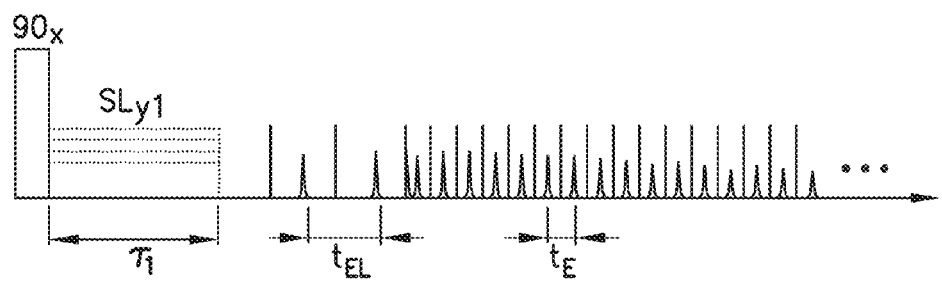
FIG. 14 is a schematic diagram illustrating an eighth embodiment of a NMR pulse sequence which can be used by the NMR spectrometer of FIG. 5A in accordance with the present application.

In a sixth embodiment, the pulse sequence of oscillating magnetic field $B_1$ that is emitted by the RF antenna 117 of the spectrometer 101 in a suite of NMR measurements carried out by the NMR Measurement module follows the pulse sequence shown in FIG. 14, which includes a 90 degree pulse in the x direction (labeled $90_x$) followed by a first spin lock pulse of a particular magnitude for a duration $\tau_1$ and then a CPMG echo excitation pulse sequence with an echo time $t_{EL}$ followed by a CMPG pulse sequence with an echo time $t_E$. Appropriate phase cycling can be carried out. The spin lock pulse duration $\tau_R$ can be varied for different values of the time delay $t_{EL}$ and $t_E$ over the suite of NMR measurements to obtain diffusion information as well as $T_2$ and $T_{1\rho}$. Experiments can be carried out with variations in the number and the value of echo delays $t_{EL}$ and $t_E$. The NMR resonance signal that follows each refocusing pulse of the CPMG echo excitation pulse sequence is digitized and stored as NMR data for each pulse sequence in the suite of NMR measurements. The NMR Data Analysis module processes such NMR data by inversion that derives three dimensional distributions functions (the first corresponding to $T_{1\rho}$ at frequency $\omega_1$, the second corresponding to $T_2$ and the third corresponding to diffusion). The inversion can utilize 3D-Inverse Laplace Transformation or other methods and also obtain just the two dimensional distributions if necessary. Such distribution functions can be analyzed to determine properties of the sample of interest.

Advantageously, the NMR experiments described herein are based on relaxation in the rotating frame that can be used to study low frequency dispersion dynamics of various systems. Many systems including but not limited to fluids in porous media, food materials, colloidal aggregation, protein dynamics and heavy oils exhibit interesting dynamics at low frequencies, especially from 1000 Hz to 100 KHz. The frequency dependence of the relaxation times in this range has unique information about system dynamics. Such information is not available by probing one single frequency and thus dispersion measurements are important. The rotating frame (or $T_{1\rho}$) based NMR experiments described herein have the potential to better evaluate the fluids and understand the slow motions due to interaction with surfaces. This implies that these pulse sequences have direct applications for fluid typing and wettability characterization. The major reason behind this is the ability to choose the applied RF and thus be able to choose various frequencies and therefore understand the clear dependence of the $T_{1\rho}$ relaxation distribution to the applied RF frequency ($\omega_1$). The NMR experiments presented herein are versatile and have the potential to be carried out in downhole oilfield applications (both for wireline and LWD), in rock core analysis at an NMR lab and at the well site.

Thus, the NMR experiments described herein can be used for separating different phases of a substance. Some examples include, adsorbed versus free shale gas or bitumen versus heavy oil and water in oil shale or bound water versus heavy oil. This act of separating NMR signal from different fluids in a mixture would help accurately gauge their respective quantities. These techniques could also help us understand the interactions between the various fluids in a mixture and also the interactions between the fluid and the enclosing matrix which yields, among others, wettability information. This could be extended to the study of the specific interaction of different constituents of the fluid with the pore/confining surfaces of medium. For example, obtaining the interaction of water and oil with the rock surface when they are both present. Such studies would help enable the modeling of residence times of different constituents of the fluid on the surface of the confining medium. The fluid in these cases could be a gas molecule interacting with the kerogen pore/inorganic pore or could be oil or water in pore. Other applications include, monitoring the aggregation state and dynamics of aggregation of various substances such as colloids, gels, or asphaltene molecules in crude oil. This could be extended to the study of the dynamics of various intra and inter-molecular interactions and to obtain viscosity of heavy oil.

In another embodiment, multidimensional relaxation diffusion experiments where $T_{1\rho}$ is at least one of the dimensions can be carried out on a downhole NMR tool with some modifications in the pulse sequence. Downhole NMR tools are generally based on permanent magnets and therefore bring up new challenges for the application of $T_{1\rho}$ based multidimensional experiments. Firstly, downhole measurements are done in grossly inhomogeneous fields. The magnetic fields of these magnets exhibit a large and complex variation of the larmor frequencies. Added to this inhomogeneous field distribution is the probable inhomogeneous fluid saturation or porosity distribution of the formation. These factors imply that inhomogeneous distributions of both the $B_0$ and $B_1$ have to be taken into account in the experiments. Such in-homogeneities result in a range of flip angles and lead to a substantial contribution to the echo formation from the off-resonant spins whose unique relaxation and diffusion behavior have to be taken into account for data analysis.

Figure 15:
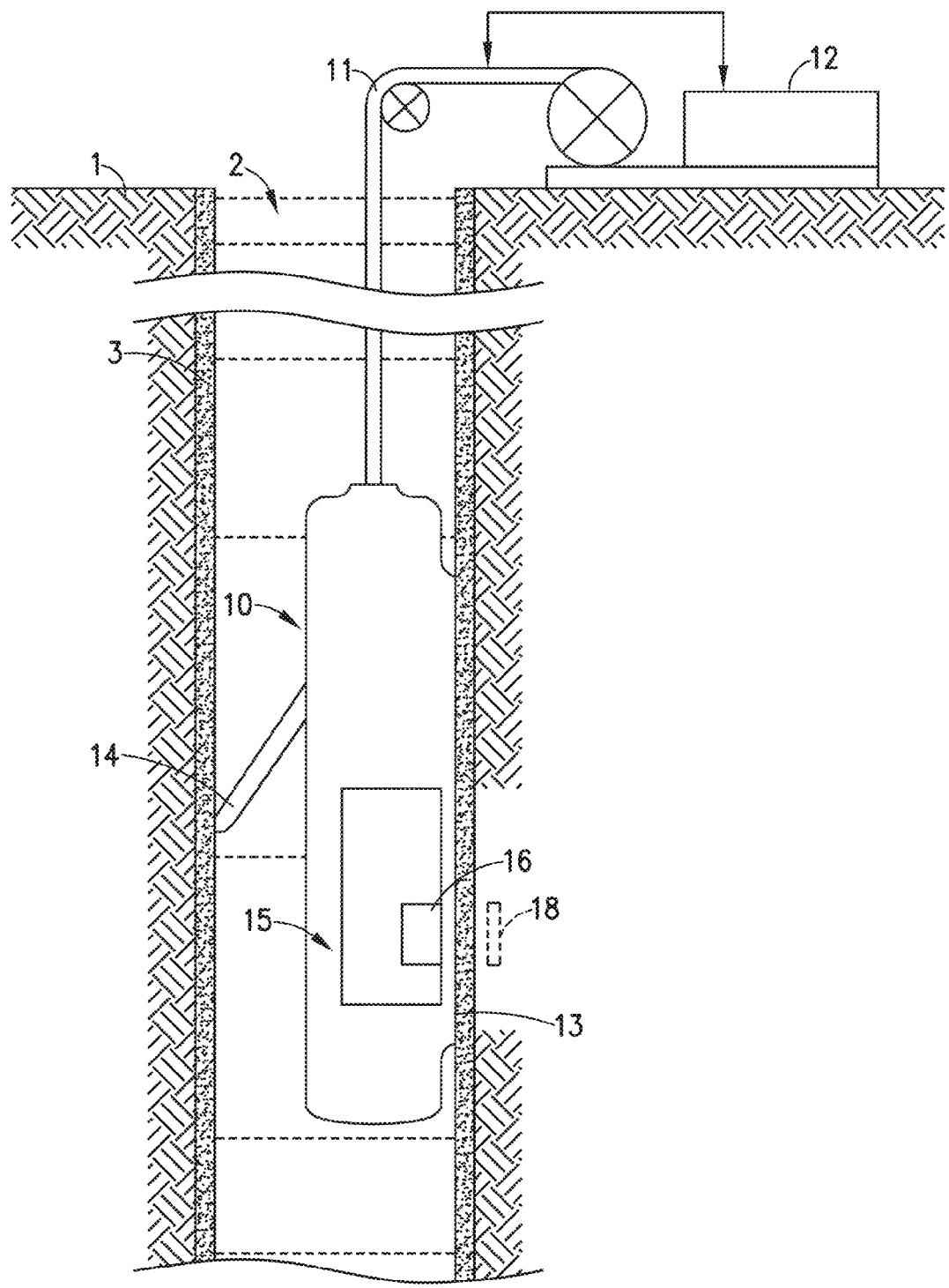
FIG. 15 shows a downhole NMR tool which can be used in practicing one or more embodiments of the present application.

FIG. 15 shows an apparatus for investigating a subsurface formation 1 traversed by a borehole 2. The borehole 2 is typically, although not necessarily, filled with a drilling fluid or mud (which contains finely divided solids in suspension) with mudcake 3 on the walls of the borehole. A downhole NMR tool 10 is suspended in the borehole 2 on an armored cable 11, the length of which substantially determines the relative depth of the logging tool 10. The cable length is controlled by suitable means at the surface such as a drum and winch mechanism (not shown). Surface equipment, represented at 12, can be of conventional type, and can include a processor subsystem and communicates with the logging tool 10. The downhole NMR tool 10 has a face 13 shaped to intimately contact the borehole wall, with minimal gaps or standoff, and a retractable arm 14 which can be activated to press the body of the downhole NMR tool 10 against the borehole wall during a logging run, with the face 13 pressed against the wall's surface. Although the downhole NMR tool 10 is shown as a single body, the tool may comprise separate components such as a cartridge, sonde, or skid, and the tool may be combinable with other logging tools. Also, while a wireline tool is illustrated, alternative forms of physical support and communicating link can be used, for example in a measurement-while-drilling system.

Figure 16:
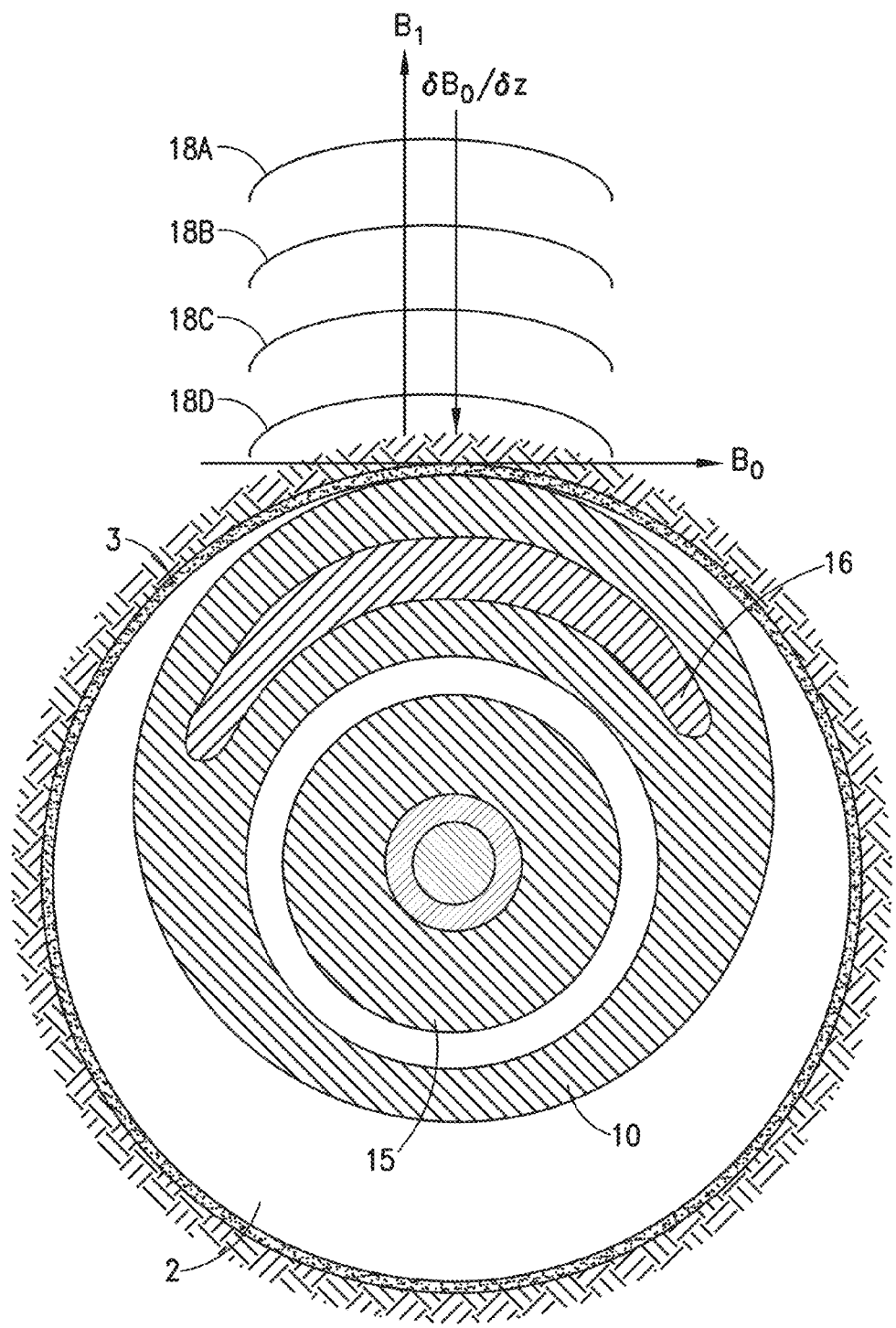
FIG. 16 is a cross-sectional view of a portion of the downhole NMR tool of FIG. 15.

In an embodiment, the downhole NMR tool 10 is based upon the MR Scanner tool available from Schlumberger Technology Corporation of Sugar Land, Tex., USA and described in U.S. Pat. No. 7,486,070. As shown in FIG. 16, the NMR tool 10 includes a permanent magnet assembly 15 as well as an array of radio frequency (RF) antennae (one shown as 16) positioned between permanent magnet assembly 15 and the wall engaging face 13. The permanent magnet assembly 15 produces a static magnetic field $B_0$ in a sample volume 18. The sample volume 18 is a region directly in front of tool face 13. Thus, during use, the sample volume 18 lies within the formation 1 as shown. The static magnetic field $B_0$ is inhomogeneous due to the design of the permanent magnet assembly 15 and thus produces a spatial magnetic field gradient ($\partial B_0/\partial z$) in the sample volume 18. The RF antenna 16 radiates, at selected times, an oscillating RF magnetic field $B_1$ having a magnetic moment substantially perpendicular (orthogonal) to that of the static magnetic field $B_0$ produced by the permanent magnet assembly 15 as indicated by the arrows shown in FIG. 16. One of ordinary skill in the art would appreciate that the same RF antenna 16 may function as a transmitter to transmit the oscillating magnetic field and as a receiver to receive the signals. Alternatively, separate transmitter and receiving antennas may be used. The tool 10 further includes electronics (not shown) that interfaces to the RF antenna 16 to carry out NMR measurements for the sample of interest in the sample volume 18. Such NMR measurements can be carried out at multiple depths of interest in thin shells, such as shells 18A, 18B, 18C, and 18D as shown. Advantages of using the tool of FIG. 16 may include, but are not limited to, the ability to assess various and multiple depths of interest, the ability to probe deeper into a rock formation, sensing of a large region, and easier tuning Though shown as being placed adjacent the borehole wall, the tool 10 may perform NMR measurements in positions offset from the borehole wall (e.g., in the center of the borehole).

The tool 10 can be configured to carry out NMR measurements as described herein in order to characterize the relaxation and/or diffusion properties of the substances of the formation and/or borehole. In one embodiment, the electronics of the tool 10 can be configured to filter the echo signal after the spinlock pulse for the selective analysis of the component of interest. For example, the on resonant component whose contribution dominates the echo amplitude can be analyzed separately.

Downhole NMR tools are generally designed to work with fixed amplitude RF pulses, even though some possibility of providing high power high bandwidth preparation pulses exist. Therefore, the amplitude of such RF pulses cannot generally be changed for the purpose of applying long spin lock pulses, which are necessary for $T_{1\rho}$ based pulse sequences. The power for the RF pulses are generally obtained from the following: downhole drilling-fluid-powered turbine-alternator system or a downhole battery system or from an up-hole generator or other power source sent via a wireline cable; or from an up-hole generator or other power source sent via wired-drill pipe or other similar mode of power transfer.

In another embodiment, the electronics of the downhole NMR tool 10 are configured to dynamically change (control) the output amplitude of the RF pulse as desired for a particular RF pulse sequence. For example, the electronics can employ resistors that change the current in the antenna circuit and/or circuitry changes to control the output of the transmitter so that the amplitude output can be controlled. Such electronics can be employed to apply spin lock pulses at various amplitudes (corresponding to various frequencies) as described herein.

Downhole NMR tools are generally constructed to work at low duty cycles. For example, the Schlumberger's CMR tool has a duty cycle of about 20%. This implies that the application of RF pulse for long periods of time to measure $T_{1\rho}$ would become challenging. Another issue to take care of for measuring $T_{1\rho}$ based measurements is the droop in the RF pulse (i.e., a drop in the pulse amplitude when applied for long periods of time) during the applications of long spin lock pulses with present day electronics. For example, the LWD-NMR tools are powered by mud flow via a turbine alternator. In one embodiment, continuous power of approximately 500-600 W is supplied from the turbine alternator. This power is used to charge a large buffer capacitor. The size of this capacitor is generally about a few thousand microfarads. For a long pulse, even if the power is a fraction of that 600 W, a droop in the RF pulse can be experienced. This can occur because (1) the rate of discharging the buffer capacitor (to output RF pulse) is faster than charging the same capacitor by turbine alternator, and (2) the amount of discharge is non-negligible to the amount of charge stored in the capacitor.

Figure 17:
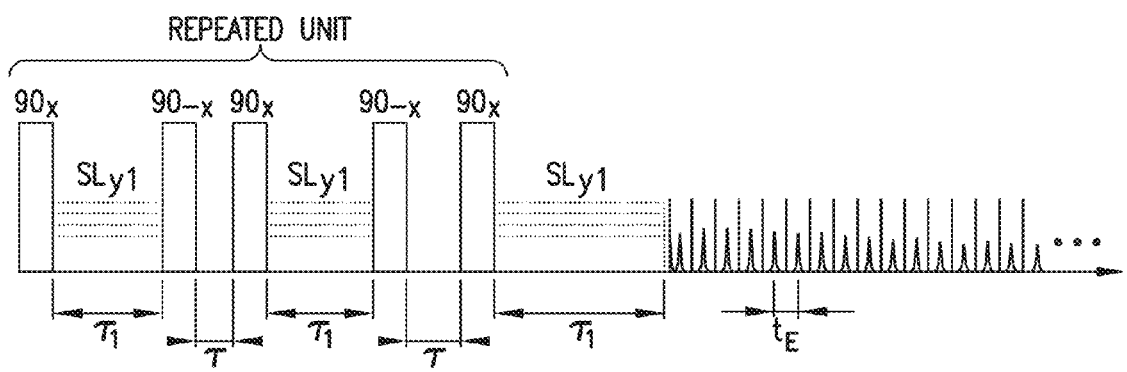
FIG. 17 is a schematic diagram illustrating a ninth embodiment of a NMR pulse sequence which can be used by a downhole NMR tool in accordance with the present application.

In another embodiment, the measurement pulse sequence produced the RF antenna of the downhole NMR tool can involve spin lock segments (labeled "$SL_{y1}$") sandwiched by intermediate segments where the magnetization is flipped to the z axis and then back to the transverse plane (in this case, by a 90-x pulse followed by a 90 x pulse) to be spin locked again as shown in FIG. 17. This enables the $T_{1\rho}$ spin lock period of the experiment to be distributed over multiple intervals (i.e., over the multiple spin lock segments $SL_{y1}$), which can reduce the requisite duty cycle of the spin lock pulses of these experiments and enable these experiments to work at lower duty cycles, especially to take care of the duty cycle and droop issues experienced by downhole NMR tools.

It is also contemplated that the pulse sequence of FIG. 17 can also be used in laboratory NMR spectrometers (such as the NMR spectrometer of FIG. 5A) in order to provide consistency with downhole NMR measurements that utilize this particular pulse sequence.

Advantageously, the $T_{1\rho}$ based pulse sequence become most interesting downhole when we are investigating samples with large dispersions. Such samples have short relaxation times at lower frequencies. Therefore applications to reduce the duty cycle in addition to their actual rotating frame relaxation times make these experiments feasible.

While particular embodiments have been described, it is not intended that the claims be limited thereto, as it is intended that the claims be as broad in scope as the art will allow and that the specification be read likewise. Thus, while particular NMR apparatus have been disclosed, it will be appreciated that other NMR apparatus (including downhole NMR tools and laboratory or bench-top NMR machines) can be used as well. For example, different permanent magnet designs, different antenna designs and different electronic designs for the NMR spectrometer can be used. Alternatively, the apparatus can spin the sample to improve the observed NMR line shapes. Furthermore, while particular inversion methodologies and data processing analysis has been described for correlating relation and diffusion information from NMR measurements, it will be understood that other inversion methodologies and data processing analysis can be similarly used. It will therefore be appreciated by those skilled in the art that yet other modifications could be made to the provided embodiments without deviating from the scope of the claims.

What is claimed is:

1. A method for analyzing a sample of interest comprising:
   (a) while applying at least a static magnetic field across a sample volume that encompasses the sample of interest, applying radio-frequency pulses of oscillating magnetic field across the sample volume, wherein the radio-frequency pulses are characterized by a component in a plane transverse to the static magnetic field, and wherein the pulses are defined by a pulse sequence that includes a plurality of measurement segments that are configured to characterize a plurality of relaxation parameters related to relaxation of nuclear magnetization of the sample of interest; and
   (b) detecting signals induced by the radio-frequency pulses of oscillating magnetic field produced in (a) in order to derive the plurality of relaxation parameters;
   wherein the plurality of measurement segments include at least one first-type measurement segment and at least one second-type measurement segment, the first-type measurement segment configured to characterize relaxation of spin-lattice interaction between nuclei of the sample of interest in a rotating frame at a predefined frequency, and the second-type measurement segment configured to characterize at least one other property of the sample of interest, the at least one other property of the sample of interest selected from the group including a relaxation property of the sample of interest in a laboratory frame and a diffusion property of the sample of interest.

2. A method according to claim 1, further comprising:
processing the signals detected in (b) by inversion to derive a plurality of distribution functions for a plurality of dimensions, wherein the plurality of dimensions correspond to a plurality of properties of the sample of interest, wherein one of the plurality of dimensions corresponds to the relaxation of spin-lattice interaction between nuclei of the sample of interest in a rotating frame at the predefined frequency.

3. A method according to claim 2, further comprising:
generating a plot based upon the plurality of distribution functions for analysis of the sample of interest.

4. A method according to claim 1, wherein:
the first-type measurement segment comprises a spin lock pulse of a particular magnitude that corresponds to the predefined frequency.

5. A method according to claim 1, wherein:
the plurality of measurements segments are configured to characterize a plurality of relaxation parameters for a set of frequencies that vary across the set.

6. A method according to claim 5, wherein:
the plurality of measurements segments further includes a plurality of first-type measurement segments that are configured to characterize relaxation of spin-lattice interaction between nuclei of the sample of interest in a rotating frame at different predefined frequencies.

7. A method according to claim 6, wherein:
one of the plurality of first-type measurement segments comprises a spin lock pulse of a particular first magnitude that corresponds to a predefined first frequency; and
another of the plurality of first-type measurement segments comprises a spin lock pulse of a particular second magnitude that corresponds to a predefined second frequency, wherein the second frequency is different than the first frequency.

8. A method according to claim 1, wherein:
the second-type measurement segment comprises a $T_2$ measurement segment configured to characterize transverse relaxation of spin-spin interaction between nuclei of the sample of interest.

9. A method according to claim 8, wherein:
the $T_2$ measurement segment comprises an echo pulse sequence for stimulating and detecting a sequence of echo pulses, wherein the echo pulse sequence has a particular echo time that defines a predefined frequency of the $T_2$ measurement segment.

10. A method according to claim 1, wherein:
the second-type measurement segment comprises a $T_1$ measurement segment configured to characterize longitudinal relaxation of spin-lattice interaction between nuclei of the sample of interest.

11. A method according to claim 10, wherein:
the $T_1$ measurement segment comprises a 90 degree pulse that follows a delay period of a predefined duration.

12. A method according to claim 1, wherein:
the second-type measurement segment comprises a diffusion measurement segment that is configured to characterize a diffusion coefficient of nuclei of the sample of interest.

13. A method according to claim 1, further comprising:
(c) repeating the operations of (a) and (b) for a suite of measurements, wherein the nuclear magnetization of the sample of interest is in equilibrium or stable condition prior to each measurement of the suite.

14. A method according to claim 13, wherein:
the plurality of measurements segments are configured to characterize a plurality of relaxation parameters for a set of frequencies that vary across the set.

15. A method according to claim 14, further comprising:
processing the signals detected in (b) by inversion to derive distribution functions for a plurality of dimensions, wherein the plurality of dimensions correspond to the plurality of relaxation parameters and associated frequencies.

16. A method according to claim 15, further comprising:
generating a plot of the distribution functions for the plurality of dimensions; and
displaying the plot for analysis of the sample of interest.

17. A method according to claim 13, further comprising:
repeating the operations of (a) and (b) for a number of suites of measurements, wherein the nuclear magnetization of the sample of interest is in equilibrium or stable condition prior to each measurement of a given suite, wherein the set of frequencies for the plurality of relaxation parameters is varied across the number of suites of measurements.

18. A method according to claim 1, wherein:
the operations of (a) and (b) are carried out in a downhole NMR tool on a sample of a subterranean formation.

19. A method according to claim 1, wherein:
the operations of (a) and (b) are carried out in a laboratory NMR tool on a sample acquired from a subterranean formation.

20. An apparatus for analyzing a sample of interest comprising:
(a) a magnet for applying at least a static magnetic field across a sample volume that encompasses the sample of interest;
(b) an RF antenna configured to produce radio-frequency pulses of oscillating magnetic field across the sample volume, wherein the radio-frequency pulses are characterized by a component transverse to the static magnetic field, and wherein the radio-frequency pulses are defined by a pulse sequence that includes a plurality of measurement segments that are configured to characterize properties of nuclear magnetization of the sample of interest; and
(c) receiver circuitry for detecting signals induced by the radio-frequency pulses of oscillating magnetic field produced by the RF antenna in order to characterize the properties of nuclear magnetization of the sample of interest;
wherein the plurality of measurement segments include at least one first-type measurement segment at least one second-type measurement segment, the first-type measurement segment configured to characterize relaxation of spin-lattice interaction between nuclei of the sample of interest in a rotating frame at a predefined frequency, and the at least one second-type measurement segment configured to characterize at least one other property of the sample of interest, the at least one other property of the sample of interest selected from the group including a relaxation property of the sample of interest in a laboratory frame and a diffusion property of the sample of interest.

21. An apparatus according to claim 20, further comprising:
a data processor for processing data derived from the signals detected by the receiver circuitry, wherein the processing of the data processor is configured to perform inversion to derive a plurality of distribution functions for a plurality of dimensions, wherein the plurality of dimensions correspond to a plurality of properties of the sample of interest, wherein one of the plurality of dimensions corresponds to the relaxation of spin-lattice interaction between nuclei of the sample of interest in a rotating frame at the predefined frequency.

22. An apparatus according to claim 21, wherein:
the data processor is configured to generate a plot based upon the plurality of distribution functions for analysis of the sample of interest.

23. An apparatus according to claim 20, wherein:
the first-type measurement segment comprises a spin lock pulse of a particular magnitude that corresponds to the predefined frequency.

24. An apparatus according to claim 20, wherein:
the second-type measurement comprises a $T_2$ measurement segment configured to characterize transverse relaxation of spin-spin interaction between nuclei of the sample of interest.

25. An apparatus according to claim 24, wherein:
the $T_2$ measurement segment comprises an echo pulse sequence for stimulating and detecting a sequence of echo pulses, wherein the echo pulse sequence has a particular echo time that defines a predefined frequency of the $T_2$ measurement segment.

26. An apparatus according to claim 20, wherein:
the second-type measurement segment comprises a $T_1$ measurement segment configured to characterize longitudinal relaxation of spin-lattice interaction between nuclei of the sample of interest.

27. An apparatus according to claim 26, wherein:
the $T_1$ measurement segment comprises a 90 degree pulse that follows a delay period of a predefined duration.

28. An apparatus according to claim 20, wherein:
the second-type measurement segment comprises a diffusion measurement segment configured to characterize a diffusion coefficient of nuclei of the sample of interest.

29. An apparatus according to claim 20, wherein:
the plurality of measurements segments are configured to characterize a plurality of relaxation parameters for a set of frequencies that vary across the set.

30. A downhole NMR tool that is conveyable within a borehole, the downhole NMR tool for analyzing a sample of interest, the downhole NMR tool comprising:
(a) a magnet for applying at least a static magnetic field across a sample volume encompassing the sample of interest;
(b) an RF antenna configured to produce radio-frequency pulses of oscillating magnetic field across the sample volume, wherein the radio-frequency pulses are characterized by a component transverse to the static magnetic field, and wherein the radio-frequency pulses are defined by a pulse sequence that includes a plurality of measurement segments that are configured to characterize properties of nuclear magnetization of the sample of interest;
(c) receiver circuitry for detecting signals induced by the radio-frequency pulses of oscillating magnetic field produced by the RF antenna in order to characterize the properties of nuclear magnetization of the sample of interest; and
(d) electronics that are configured to vary amplitude of the radio-frequency pulses produced by the RF antenna.

31. A downhole NMR tool according to claim 30, wherein:
the electronics are configured to dictate amplitude of a spin lock pulse produced by the RF antenna in order to characterize relaxation of spin-lattice interaction between nuclei of the sample of interest in a rotating frame at a predefined frequency corresponding the amplitude of the spin lock pulse.

32. A downhole NMR tool according to claim 30, wherein:
the radio-frequency pulses produced by the RF antenna include a plurality of spin lock segments sandwiched by intermediate segments where the magnetization is flipped to the z axis and then back to the transverse plane.

33. A downhole NMR tool according to claim 32, wherein:
the plurality of spin lock segments and the intermediate segments are repeated over a suite of measurements, wherein the nuclear magnetization of the sample of interest is in equilibrium or stable condition prior to each measurement of the suite.

34. A method for analyzing a sample of interest comprising:
(a) while applying at least a static magnetic field across a sample volume that encompasses the sample of interest, applying radio-frequency pulses of oscillating magnetic field across the sample volume, wherein the radio-frequency pulses are characterized by a component in a plane transverse to the static magnetic field, and wherein the pulses are defined by a set of pulse sequences that include measurement segments configured to characterize relaxation of spin-lattice interaction between nuclei of the sample of interest in a rotating frame at a number of predefined frequencies; and
(b) detecting signals induced by the radio-frequency pulses of oscillating magnetic field produced in (a) in order to derive a relaxation property of the sample of interest in the rotating frame for the number of predefined frequencies;
(c) processing the signals detected in (b) by inversion to derive a plurality of distribution functions for a plurality of dimensions, wherein the plurality of dimensions correspond to the relaxation property of the sample of interest in the rotating frame for the number of predefined frequencies; and
(d) generating a plot based upon the plurality of distribution functions derived in (c) for analysis of the sample of interest.

* * * * *